(12) United States Patent
Jones

(10) Patent No.: US 11,565,081 B1
(45) Date of Patent: Jan. 31, 2023

(54) CATHETER AND SYSTEMS FOR PROVIDING RADIAL ARTERY ACCESS OF AT LEAST ONE OF A CONTRALATERAL SUBCLAVIAN ARTERY AND AN INTERNAL MAMMARY ARTERY OF A PATIENT FOR DIAGNOSTIC AND INTERVENTIONAL ANGIOGRAPHY

(71) Applicant: Phillip Eugene Jones, Sebring, FL (US)

(72) Inventor: Phillip Eugene Jones, Sebring, FL (US)

(*) Notice: Subject to any disclaimer, the term of this patent is extended or adjusted under 35 U.S.C. 154(b) by 0 days.

(21) Appl. No.: 17/702,502

(22) Filed: Mar. 23, 2022

Related U.S. Application Data

(60) Provisional application No. 63/236,706, filed on Aug. 25, 2021.

(51) Int. Cl.
| | |
|---|---|
| *A61M 25/09* | (2006.01) |
| *A61M 25/00* | (2006.01) |
| *A61M 5/00* | (2006.01) |
| *A61M 25/01* | (2006.01) |
| *A61M 25/06* | (2006.01) |

(52) U.S. Cl.
CPC ........ *A61M 25/0068* (2013.01); *A61M 5/007* (2013.01); *A61M 25/0136* (2013.01); *A61M 25/09* (2013.01); *A61M 2025/0681* (2013.01); *A61M 2210/125* (2013.01)

(58) Field of Classification Search
CPC .......... A61M 25/0068; A61M 25/0041; A61M 2025/0681
See application file for complete search history.

(56) References Cited

U.S. PATENT DOCUMENTS

| 547,645 | A | | 10/1895 | Lacroix | |
|---|---|---|---|---|---|
| 5,876,385 | A | * | 3/1999 | Ikari | A61M 25/0041 604/523 |
| 5,916,209 | A | * | 6/1999 | Mick | A61M 25/0041 604/523 |
| 6,638,268 | B2 | * | 10/2003 | Niazi | A61M 25/0662 604/528 |
| 8,100,883 | B1 | * | 1/2012 | Johnson | A61M 25/0041 604/523 |
| 10,258,785 | B2 | | 4/2019 | Mide | |

(Continued)

*Primary Examiner* — Laura A Bouchelle
(74) *Attorney, Agent, or Firm* — Derek Fahey, Esq.; The Plus IP Firm, PLLC

(57) ABSTRACT

A catheter for radial artery access to the contralateral subclavian artery and internal mammary artery is disclosed. The catheter includes a preformed tubular hook element configured for aligning coaxially within the subclavian artery from a radial access. The tubular hook element includes a first arm connected to a second arm via a curved element, and a second arm connected, via a second curved element, to an elongated tubular body. Each curved element has an angle between approximately 90-130 degrees. The catheter can receive a second catheter and guide it to further advance the subclavian artery. The second catheter then extends past distal end of the catheter and advances into the internal mammary arteries for selective angiography and intervention. The two-catheter system allows angiography and intervention of the entire right and left upper extremities to be performed depending on the access from the left or right radial artery, respectively.

19 Claims, 29 Drawing Sheets

(56) References Cited

U.S. PATENT DOCUMENTS

2003/0036698 A1* 2/2003 Kohler .............. A61M 25/0041
600/435
2015/0112307 A1 4/2015 Margolis

* cited by examiner

CATHETER AND SYSTEMS FOR PROVIDING RADIAL ARTERY ACCESS OF AT LEAST ONE OF A CONTRALATERAL SUBCLAVIAN ARTERY AND AN INTERNAL MAMMARY ARTERY OF A PATIENT FOR DIAGNOSTIC AND INTERVENTIONAL ANGIOGRAPHY

CROSS-REFERENCE TO RELATED APPLICATIONS

This application claims the benefit of the filing date of U.S. Provisional Application Ser. No. 63/236,706 titled "Catheter and Systems for Providing Radial Artery Access of at Least One of a Contralateral Subclavian Artery and an Internal Mammary Artery of a Patient for Diagnostic and Interventional Angiography" and filed Aug. 25, 2021, and the subject matter of which is incorporated herein by reference.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

TECHNICAL FIELD

The present disclosure relates to the field of medical devices, and more specifically to the field of catheters used for coronary angiography.

BACKGROUND

Coronary angiography is a procedure that uses dye in the arteries and x ray imaging to detect blockages within the coronary arteries that can be caused by plaque buildup. When coronary angiography is performed, the physician inserts a catheter tube into the patient's blood vessel to inject the contrast dye. When the procedure is complete, the physician removes the catheter and then establishes hemostasis. When a physician discovers a blockage in the vessel, they may use percutaneous coronary intervention to resolve the blockage and create better blow flow within the vessel.

The traditional access point for coronary angiography and intervention was via the femoral arteries; however, femoral artery access is no longer the default strategy for modern and progressive coronary and vascular diagnosticians and interventionists. Within the last ten years, the preferred method for coronary angiography and intervention access within the United States has changed to radial artery access. The switch to radial artery access is beneficial to both the patients and the physicians performing the angiography. The benefit of radial artery access includes it is safer than femoral access, patients prefer radial access because recovery and return to function is quicker, radial access is less uncomfortable to the patient and radial access costs significantly less for the patient. Care of the site post procedure is simpler for both the patient and the physicians treating the site. The practice of radial access was the standard of care in most of the world prior to the United States. As the United States adopted the practice of using radial access, equipment design and availability of this new equipment has rapidly evolved.

Most of the basic problems and challenges have been solved during the rapid evolution. Subclavian and internal mammary artery angiography and intervention is one such problem that was not able to be solved during the initial evolution of the equipment. Issues exist for cardiologists and vascular interventionists when subclavian and internal mammary artery access is necessary for angiography and intervention.

The left subclavian and internal mammary arteries cannot be reliably or effectively accessed with the current equipment and methods during radial access from the right upper extremity. Similarly, accessing the right subclavian and internal mammary arteries cannot be reached reliably from the left forearm access. These issues with access limit preferred safe access options when for any variety of common clinical reasons either the right or left radial artery may be unavailable. Often, if the preferred safe access option is unavailable, cardiologists and vascular interventionists revert to a femoral access to solve the dilemma. This reversion reduces patient satisfaction, patient safety, and is a greater cost.

As a result, there exists a need for improvements over the prior art and more particularly for a more efficient and reliable way of providing access to the subclavian and internal mammary arteries during coronary angiography and intervention.

SUMMARY

A catheter and system for providing radial artery access of at least one of a contralateral subclavian artery and an internal mammary artery of a patient for diagnostic and interventional angiography is disclosed. This Summary is provided to introduce a selection of disclosed concepts in a simplified form that are further described below in the Detailed Description including the drawings provided. This Summary is not intended to identify key features or essential features of the claimed subject matter. Nor is this Summary intended to be used to limit the claimed subject matter's scope.

In one embodiment, a catheter for providing radial artery access of at least one of a contralateral subclavian artery and an internal mammary artery of a patient for diagnostic and interventional angiography, wherein the catheter is for introducing a second catheter into the patient is disclosed. The system includes an elongated tubular body having a distal end portion and a proximal end portion. The catheter has a preformed tubular hook element extending from the distal end portion of the elongated tubular body. The preformed tubular hook element is defined by a first arm proximal to a terminating end of the catheter. A curve connects the first arm to a second arm, and a second curve connects the second arm to the distal end portion of the elongated tubular body. A first longitudinal axis of the arm is disposed at a first angle of between approximately 90-130 degrees relative to a second longitudinal axis of the second arm. A second longitudinal axis of the second arm is disposed at a second angle of between approximately 90-130 degrees relative to a third longitudinal axis of the elongated tubular body. The catheter further includes a torquing element disposed at the proximal end portion of the elongated tubular body and a lock hub at the proximal end portion of the elongated tubular body.

Additional aspects of the disclosed embodiment will be set forth in part in the description which follows, and in part will be obvious from the description, or may be learned by practice of the disclosed embodiments. The aspects of the disclosed embodiments will be realized and attained by means of the elements and combinations particularly pointed out in the appended claims. It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute part of this specification, illustrate embodiments of the invention and together with the description, explain the principles of the disclosed embodiments. The embodiments illustrated herein are presently preferred, it being understood, however, that the invention is not limited to the precise arrangements and instrumentalities shown, wherein.

DETAILED DESCRIPTION

Figure 1A:
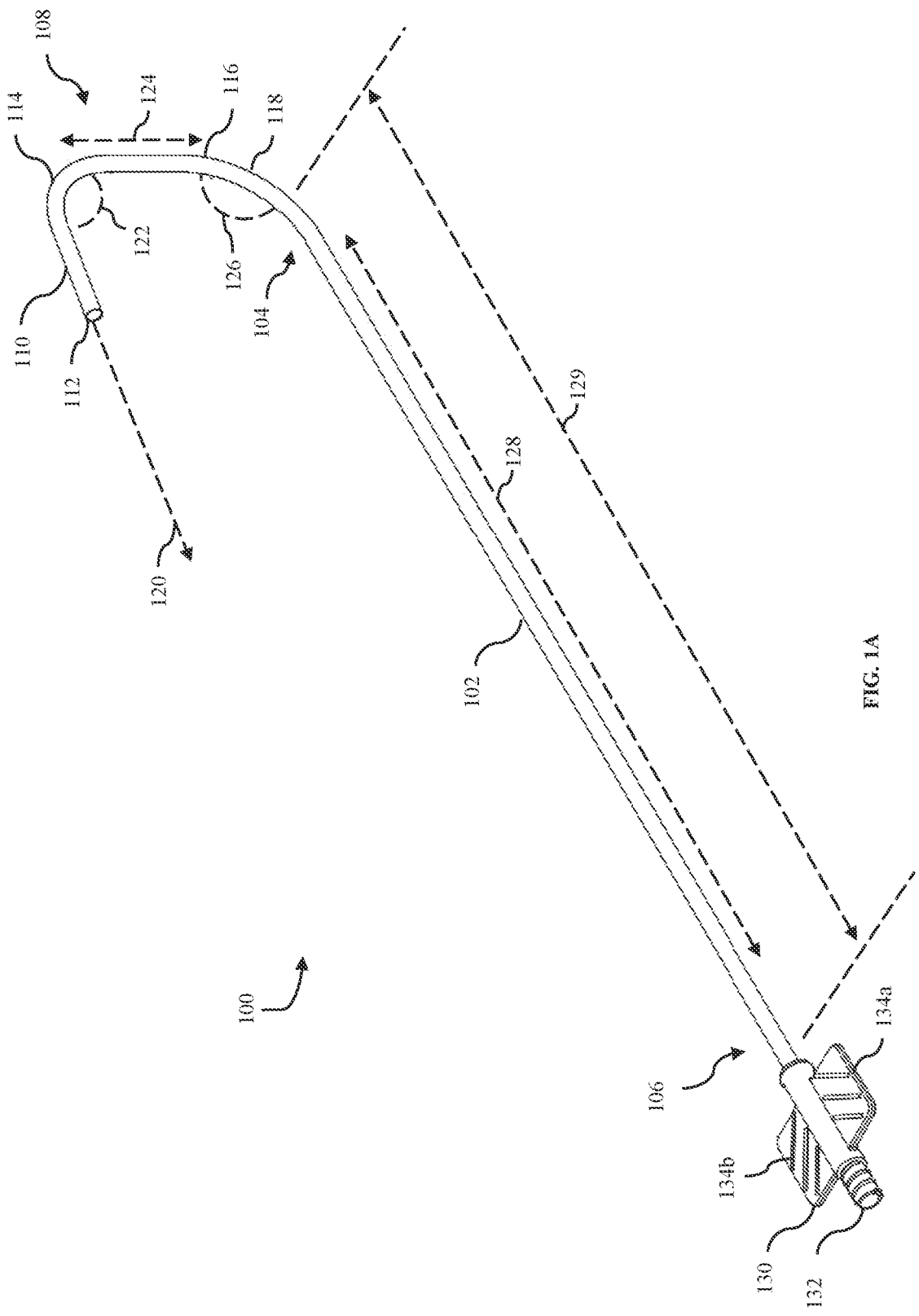
FIG. 1A is a perspective view of a catheter for subclavian artery access, according to an example embodiment.

The following detailed description refers to the accompanying drawings. Whenever possible, the same reference numbers are used in the drawings and the following description to refer to the same or similar elements. While disclosed embodiments may be described, modifications, adaptations, and other implementations are possible. For example, substitutions, additions, or modifications may be made to the elements illustrated in the drawings, and the methods described herein may be modified by substituting, reordering, or adding additional stages or components to the disclosed methods and devices. Accordingly, the following detailed description does not limit the disclosed embodiments. Instead, the proper scope of the disclosed embodiments is defined by the appended claims.

The disclosed embodiments improve upon the problems with the prior art by providing a system providing radial artery access of at least one of a contralateral subclavian artery and an internal mammary artery of a patient for diagnostic and interventional angiography. The system provides reliable and efficient access into the left subclavian and internal mammary arteries during coronary and vascular angiography and interventions, namely, radial coronary angiography via radial or ulnar artery access procedures. The left subclavian and internal mammary arteries cannot be reliably and effectively be sub-selectively cannulated from the right upper extremity for diagnostic angiography, much less for intervention and stenting. Likewise, the right subclavian and internal mammary arteries cannot reliably be reached from the left forearm access during radial access coronary angiography. For a variety of common clinical reasons, either the right or left radial artery may be preferred in a particular patient or may be unavailable thereby limiting preferred safe access options to the subclavian and internal mammary arteries. Therefore, the present disclosure eliminates the need for coronary and vascular angiographers and interventionists to revert to performing angiography through the femoral artery. As a result, the catheter system disclosed herein improves upon the prior art by reducing patient costs associated with coronary angiography procedures by allowing the procedure to be performed through radial artery access, reducing the risks associated with angiography procedure, increasing procedural options for patients, and increases the overall satisfaction and well-being of patients.

Additionally, the catheter system improves upon the prior art by allowing for angiography and intervention of the entire right upper extremity arteries from the left radial access, including but not limited to the right brachiocephalic artery, right subclavian artery, and the right carotid artery. The catheter system also allows the angiography and intervention of the entire left upper extremity arteries from the right radial access, including but not limited to, the left subclavian artery, left vertebral artery, left carotid artery, bilateral renal arteries, mesenteric arteries, and the bilateral iliac and femoral arteries.

Figure 1B:
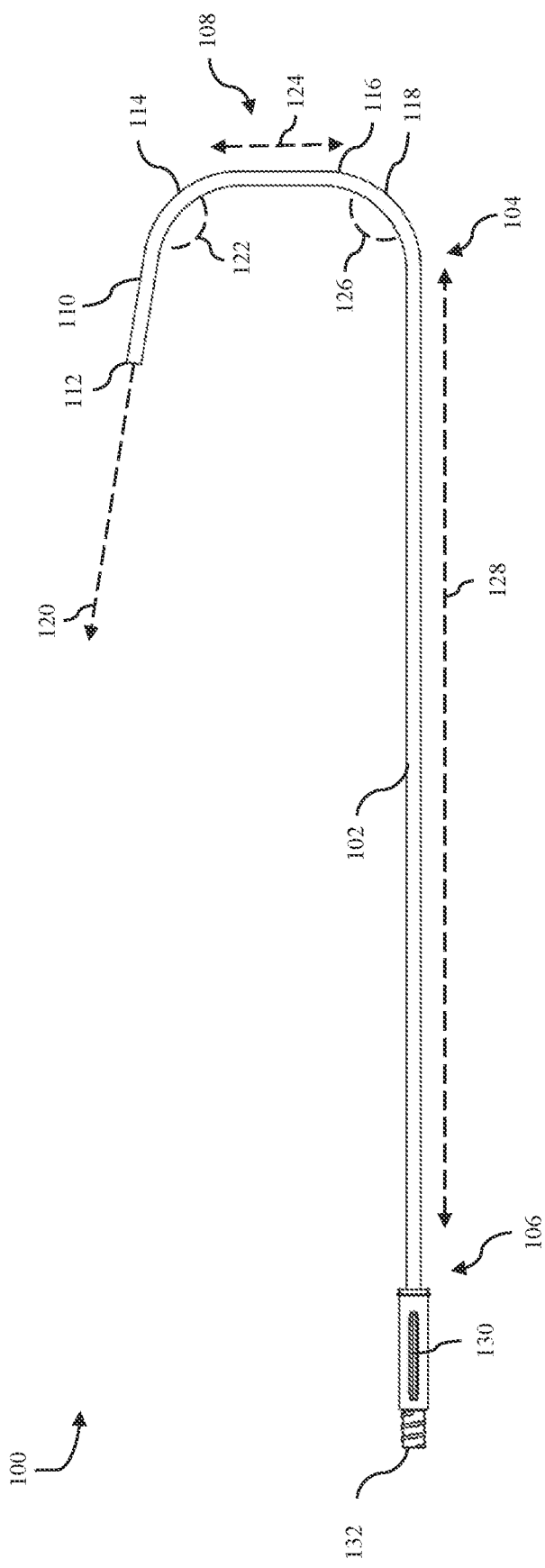
FIG. 1B is a side view of the catheter for subclavian artery access, according to an example embodiment.

Referring now to the Figures, FIG. 1A and FIG. 1B are views of a catheter 100 for subclavian artery access, according to an example embodiment. FIG. 1A is perspective view of the catheter for subclavian artery access, according to an example embodiment. FIG. 1B is a side view of the catheter for subclavian artery access, according to an example embodiment. The catheter incudes an elongated tubular body 102 having a distal end portion 104 and a proximal end portion 106. The catheter enters the patient such that the distal end portion enters the patient while the proximal end portion stays outside of the patient. A preformed tubular hook element 108 extends from the distal end portion of the elongated tubular body. The preformed tubular hook element is defined by a first arm 110 proximal to a terminating end 112 of the catheter, a curve 114 connecting the first arm to a second arm 116, and a second curve 118 connecting the second arm to the distal end portion of the elongated tubular body. The preformed tubular hook element has a hook shape configured to fit in the into the subclavian artery while positioned in the aorta of the heart. The first arm enters the subclavian artery while the second arm is positioned in the aorta. The first arm has a first longitudinal axis 120 disposed at a first angle 122 relative to a second longitudinal axis 124 of the second arm. The first angle has an arc angle of between 90 degrees and 130 degrees relative to the second longitudinal axis of the second arm. The first arm has a length between 3 centimeters and 5 centimeters. Likewise, the second longitudinal axis of the second arm is disposed at a second angle 126 relative to a third longitudinal axis 128 of the elongated tubular body. The second angle has an arc angle of between 90 degrees and 130 degrees relative to the third longitudinal axis. The second arm has a length between 2 centimeters and 7 centimeters depending. The system further includes a torquing element 130 disposed at the proximal end portion of the elongated tubular body and a lock hub 132 at the proximal end portion of the elongated tubular body. In one embodiment, the torquing element may include a pair of torquing wings (134a, 134b), wherein each wing extends radially from an exterior of the elongated tubular body. The size of both the first arm and the second arm may vary depending on the physical characteristics of the patient; however, the lengths remain within the specified ranges. The elongated tubular body has an elongated tubular body length 129 of approximately 78 centimeters to 80 centimeters. The elongated tubular body also has a lumen. The elongated tubular body length and the lengths of the first arm and second arm have a combined length of approximately 90 centimeters to 100 centimeters. The outer diameter of the catheter is approximately 2.08 millimeters. The inner diameter of the catheter is approximately 1.8 millimeters.

The elongated tubular body 102 and the preformed tubular hook element are flexible and narrow tubes that allows the catheter to be maneuvered through the arteries of a patient. The elongated tubular body and preformed tubular hook element are made of soft flexible plastics configured to allow the catheter to maneuver through the arteries of the patient's body. The elongated tubular body and preformed tubular hook element are soft such that the catheter will not damage the arteries or vessels during procedure.

In certain embodiments, the first angle 122 is more optimally between approximately 90 degrees and 120 degrees, and the first arm has a first arm length of at least 4 centimeters. In other embodiments, the second angle 126 is more optimally between approximately 100 degrees and 120 degrees, and the second arm has a second arm length between 3 cm to 6 cm. The catheter has an outer diameter of approximately between 1.58 millimeters 2.58 millimeters and an inner diameter of approximately 1.30 millimeters and 2.3 millimeters. The first angle and second angle of the catheter allows the catheter to effectively fall into the opening of the subclavian artery when withdrawn during coronary angiography procedure described herein. The angle of first arm and the angle of the second arm, and the length of the first arm and the second arm, corresponds to the dimensions of the subclavian artery such that the catheter can be positioned coaxially within the artery. The catheter is aligned coaxially within the artery such that the catheter is positioned in the same direction and along the same axis as the artery.

Figure 2A:
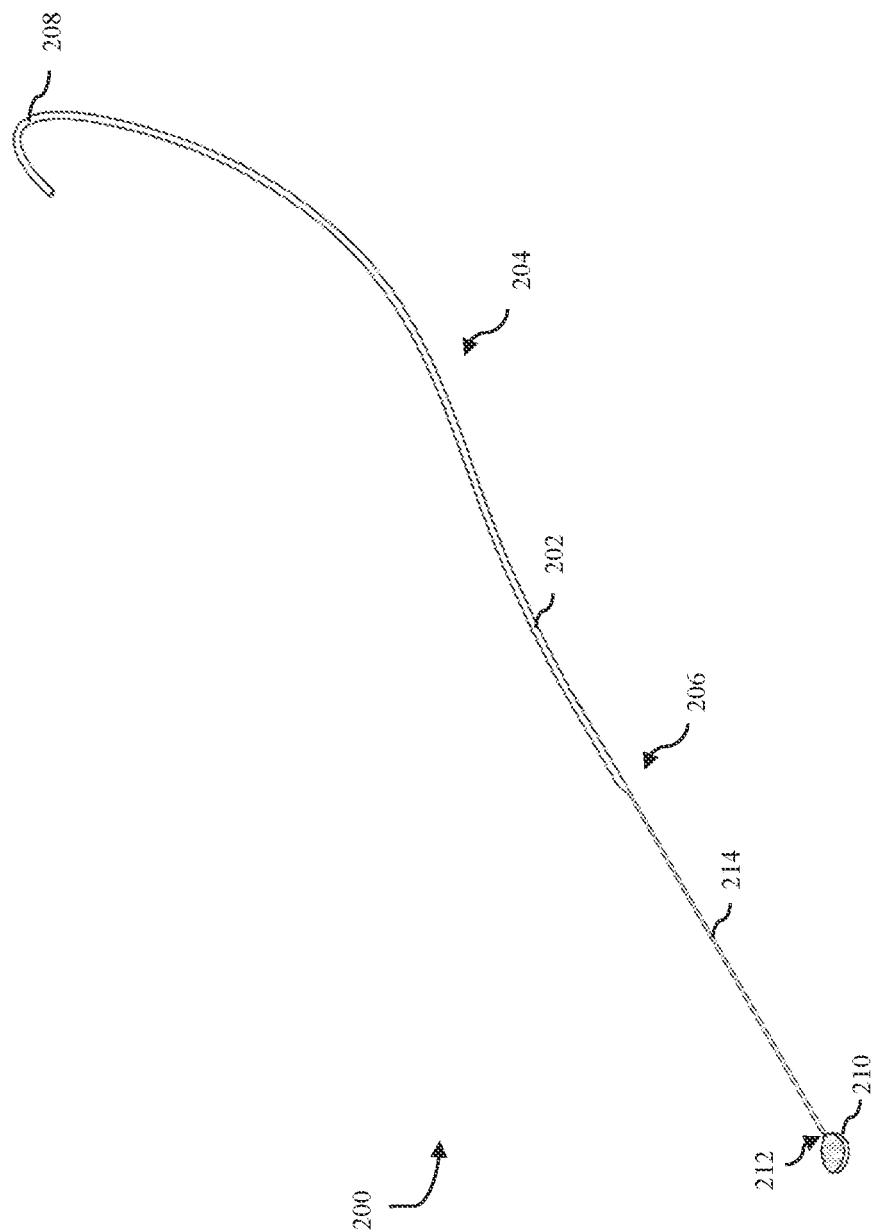
FIG. 2A is a perspective view of a second catheter for internal mammary intubation catheter extensions, according to an example embodiment.
Figure 2B:
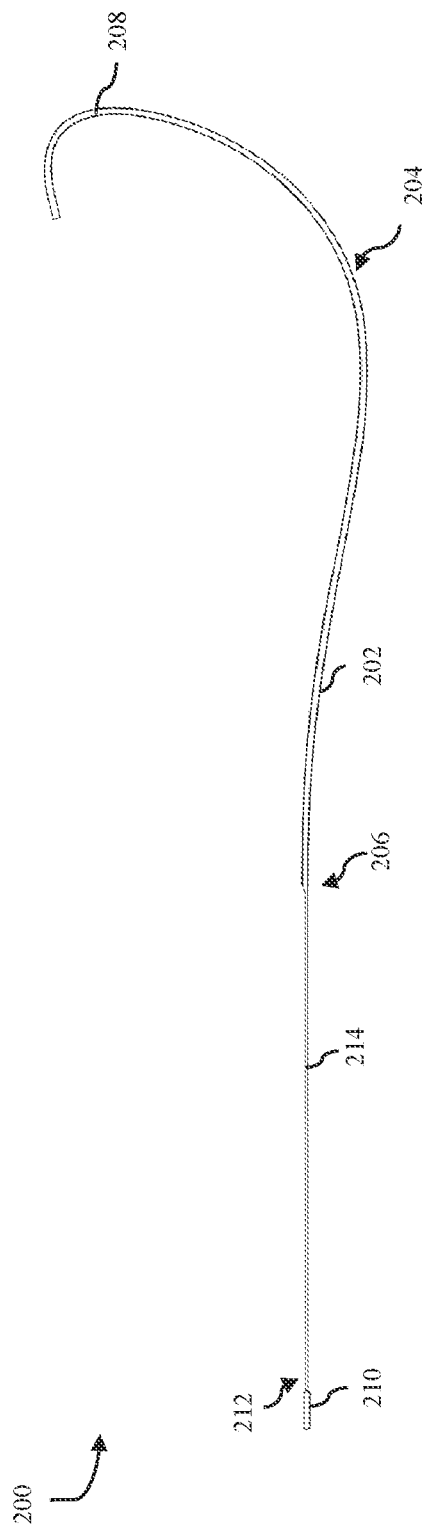
FIG. 2B is a side view of the second catheter for internal mammary intubation catheter extensions, according to an example embodiment.

Referring now to FIG. 2A and FIG. 2B, views of a second catheter for internal mammary intubation catheter extensions are shown, according to an example embodiment. FIG. 2A is a perspective view of a second catheter for internal mammary intubation catheter extensions, according to an example embodiment. FIG. 2B is a side view of a second catheter for internal mammary intubation catheter extensions, according to an example embodiment.

The second catheter 200 has a second catheter elongated tubular body 202 having a second catheter distal end portion 204 and a second catheter proximal end portion 206. A second preformed tubular hook element 208 extends from the second catheter distal end portion. The second catheter further includes a torquing element 210 disposed proximal to a second catheter proximal terminating end 212. The torquing element is flat where the torquing element is in attachment with an elongated shaft 214. The elongated shaft is disposed between the second catheter proximal terminating end and the second catheter proximal end portion. In certain embodiments, the torquing element may include a pair of wings extending from the perimeter of the second catheter. However, other embodiments, such as a knob, bulb, or other elements that may use to maneuver and rotate the second catheter may be used and is within the spirit and scope of the present invention. The second preformed tubular hook element is configured to pass through the lumen of the catheter.

In certain embodiments, the second catheter has a second catheter length of approximately 110 centimeters. The second catheter has a length longer than that of the catheter (illustrated in FIG. 1) because it is configured to pass through the catheter and extend beyond the catheter to advance into the internal mammary arteries. The elongated shaft of the second catheter has a shaft length of approximately 50 centimeters to 70 centimeters. Additionally, the second catheter may include a lubricous coating covering at least a portion of the second catheter exterior of the second catheter for reducing friction between the second catheter exterior and a lumen wall of the catheter.

In certain embodiments, the second catheter 200 is substantially tubular such that the second catheter proximal end portion is a solid shaft and has a flat torquing element disposed proximal to a second catheter proximal terminating end and the second catheter elongated tubular body is hollow such that it can receive an exchange wire and fluid. The second catheter has an outer diameter of approximately between 1.2 millimeters 2.2 millimeters and an inner diameter of approximately 0.92 millimeters and 1.92 millimeters.

The catheter 100 and second catheter 200 may be made from soft flexible plastics configured to maneuver through the arteries of the patient's body. The catheter is soft such that it will not puncture the artery or vessels during procedure. In other embodiments, the catheter and second catheter may also made from a variety of materials such as vinyl, including polyvinyl chloride, red rubber latex, silicone, polytetrafluoroethylene, and certain catheters manufactured without DEHP, a chemical plasticizer. The catheter and second catheter may include layered materials having a mesh layer. The meshed layer may be stainless steel mesh between a layer of polytetrafluoroethylene and a layer of polyester elastomer for example. The mesh layer may be between other materials of the catheter consistent with this disclosure. The mesh layer is configured to compress when the torquing element is engaged, thereby bending tubular hook elements at the optimal angle to align coaxially within the vessel.

Referring now to the catheters disclosed in FIG. 1A through FIG. 2B, a system for providing radial artery access of a contralateral subclavian artery and an internal mammary artery of a patient for diagnostic and interventional angiography comprising a catheter and a second catheter, where the catheter is for introducing the second catheter into the patient, the catheter system comprises the catheter of FIG. 1A and the second catheter of FIG. 2A. A method for utilizing the catheter system during coronary angiography and intervention procedures is as described herein, according to an example embodiment.

The following description details the use and application of the two-catheter system in medical practice according to an example embodiment. It is understood that the system may be used in medical practice through the left or right radial arteries. In an example embodiment, to perform coronary angiography and interventional procedures, generally a 0.035 exchange wire is used and inserted into the patient. The present invention improves upon the prior art by allowing the procedures to be performed from the right radial access point such that the system is advanced into the ascending aorta. Other sized exchange wires may be used according to standard medical practice and are within the spirit and scope of the disclosure.

Once in the ascending aorta, using general techniques, the exchange wire is then directed into the proximal descending aorta. The catheter (illustrated in FIG. 1A) is tubular shaped such that it is configured to receive and pass over the exchange wire. The catheter is guided over the exchange wire and advanced into the proximal descending aorta beyond the ostium of the left subclavian artery. The catheter is then purged, cleared, and connected in accordance with standard medical practice. In some embodiments, the use of a Touhy-Borst device is used to prevent backflow of fluid in the catheter. Then the catheter is slowly withdrawn until is falls into the left subclavian ostium such that the first arm advances into the left subclavian artery. The exchange wire is then advanced antegrade into the subclavian artery. The catheter is then either advanced or withdrawn a few millimeters to position the catheter in the vessel coaxially in the right to left projection such that the first arm is positioned coaxially to the left subclavian artery. By rotating the torquing element 130, the first arm 110 and the second arm 116 are rotated to position either catheter anterior or posterior artery. Specifically, the mesh layer compress within the curve 114 and second curve 118 to achieve the optimal angle. The angle of first arm and the angle of the second arm, and the length of the first arm and the second arm, corresponds to the dimensions of the subclavian artery such that the catheter can be positioned coaxially within the artery. The catheter is aligned coaxially within the artery such that the catheter is positioned in the same direction and along the same axis as the artery. The exchange wire is then removed. The catheter is then purged, cleared, and connected in accordance with standard medical practice. Now, selective angiography and intervention of at least one of the left subclavian, axillary, and the left vertebral arteries can be performed in accordance with standard procedure. Selective angiography and intervention can be performed on the entire left upper extremity from this position. In other embodiments, angiography and intervention can be performed on the abdominal, iliac, and femoral arteries.

To sub-selectively cannulate the left internal mammary artery, the exchange wire is re-inserted into the catheter and advanced out into the distal subclavian artery. A Touhy-Borst device is used to prevent backflow of fluid in the catheter. In some example embodiments, the catheter for subclavian artery access (illustrated in FIG. 1) includes a lock hub. The lock hub 132 is configured to attach a Touhy-Borst device to the catheter. The lock hub may include threading to engage a Touhy-Borst device, other attachment, or another catheter. The second catheter for internal mammary intubation (illustrated in FIG. 2A) is inserted into the patient through the radial artery access. The second catheter receives the exchange wire such that the catheter is inserted into the patient over the exchange wire and through the catheter for subclavian artery access. The second catheter is then advanced into the left subclavian artery extending beyond the terminal end of the catheter for subclavian artery access. The second catheter is advanced within the left subclavian artery beyond the left internal mammary artery ostium. By rotating the torquing element 210, the second preformed tubular hook element 208 is rotated to position either catheter anterior or posterior to effectively intubate the ostium of the left internal mammary artery. The exchange wire is then removed. The catheter is then purged, cleared, and connected in accordance with standard medical practice. Now, selective angiography and intervention of the left internal mammary artery can be performed in accordance with standard procedure.

The methods for utilizing the catheter system during coronary angiography and intervention procedures for left radial access to the right subclavian, right internal mammary artery, and the right carotid artery is within the spirt and scope of the disclosure and is a reflective procedure of the aforementioned method, according to the example embodiment.

Figure 3A:
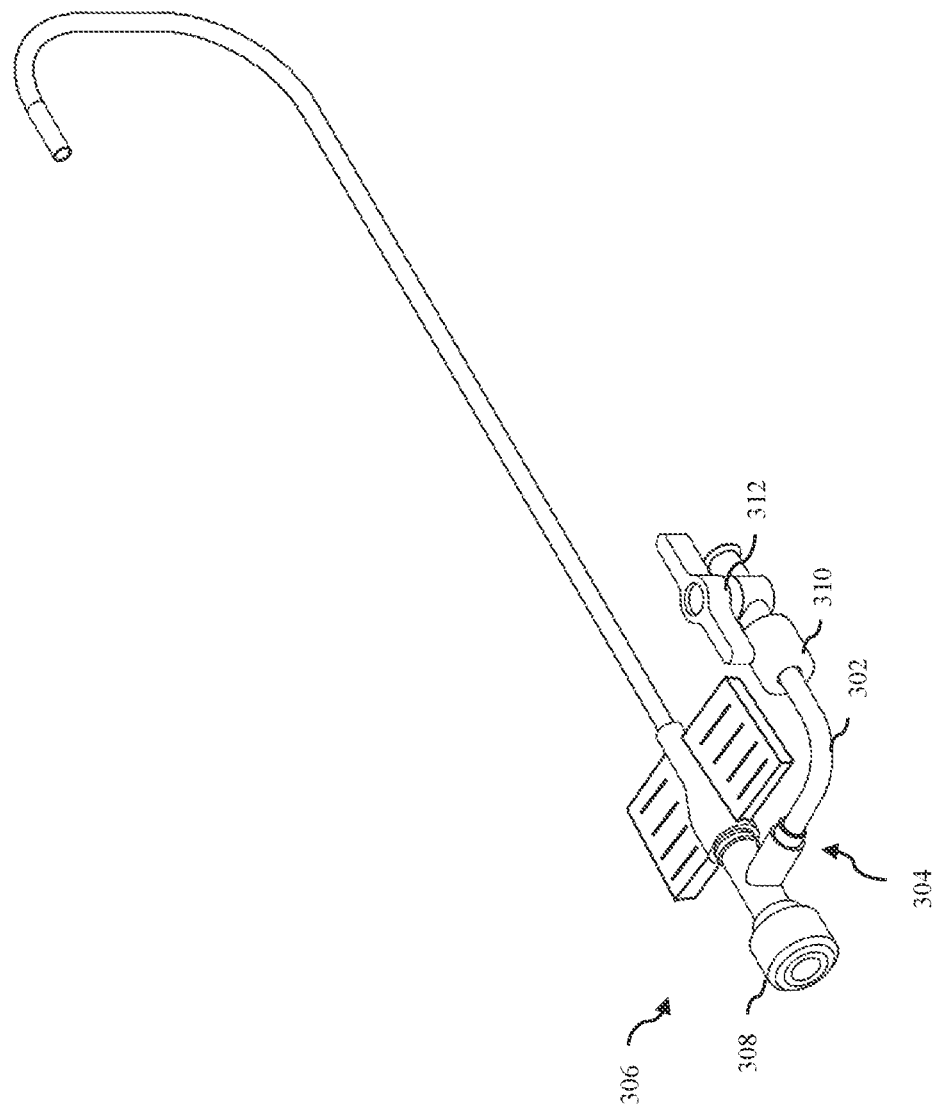
FIG. 3A is a perspective view of the catheter for subclavian artery access, according to a second example embodiment.
Figure 3B:
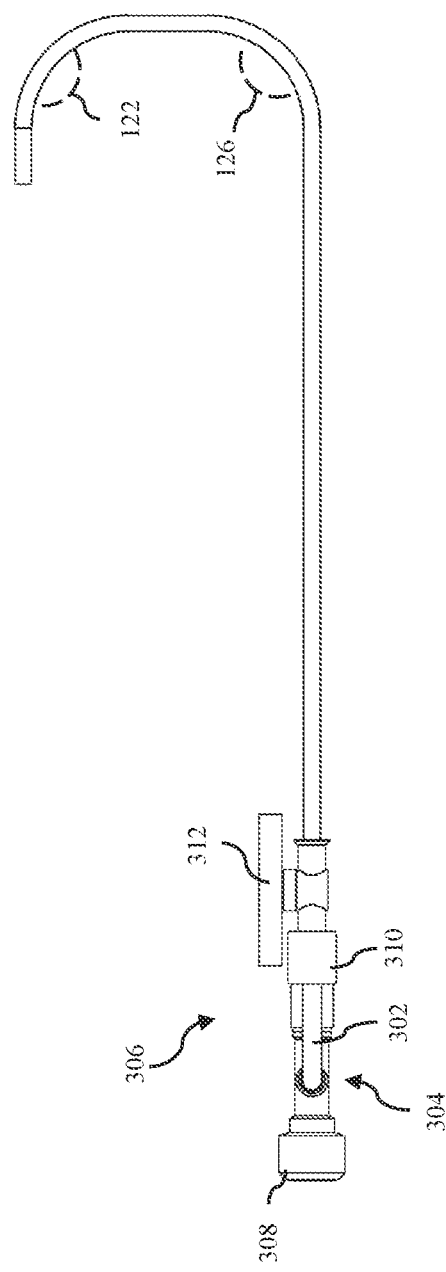
FIG. 3B is a side view of the catheter for subclavian artery access, according to a second example embodiment.

Referring now to FIG. 3A and FIG. 3B, a perspective view and a side view of a catheter for subclavian artery access is shown, according to a second example embodiment. FIG. 3A is a perspective view of a catheter for subclavian artery access, according to a second example embodiment. FIG. 3B is a side view of a catheter for subclavian artery access, according to a second example embodiment. The catheter may further include a second elongated tubular body 302. The second elongated tubular body has a second elongated tubular body lumen 304 connected to the proximal end portion 306 of the elongated tubular body such that the second elongated tubular body lumen is in fluid communication with a first elongated tubular body lumen of the elongated tubular body. The second elongated tubular body is in fluid communication with the elongated tubular body such that the tubular opening is continuous between the elongated bodies to allow materials or fluids to pass through the catheter. The catheter has a hemostatic diaphragm 308 disposed at the proximal end portion of the elongated tubular body. The hemostatic diaphragm or hemostasis valve is in attachment with the hub of the catheter. The second elongated tubular body lumen may also include at lock hub 310. The lock hub may be in attachment with a stop cock 312 where the stop cock is an externally operated valve regulating the flow of a liquid through the catheter.

Figure 4A:
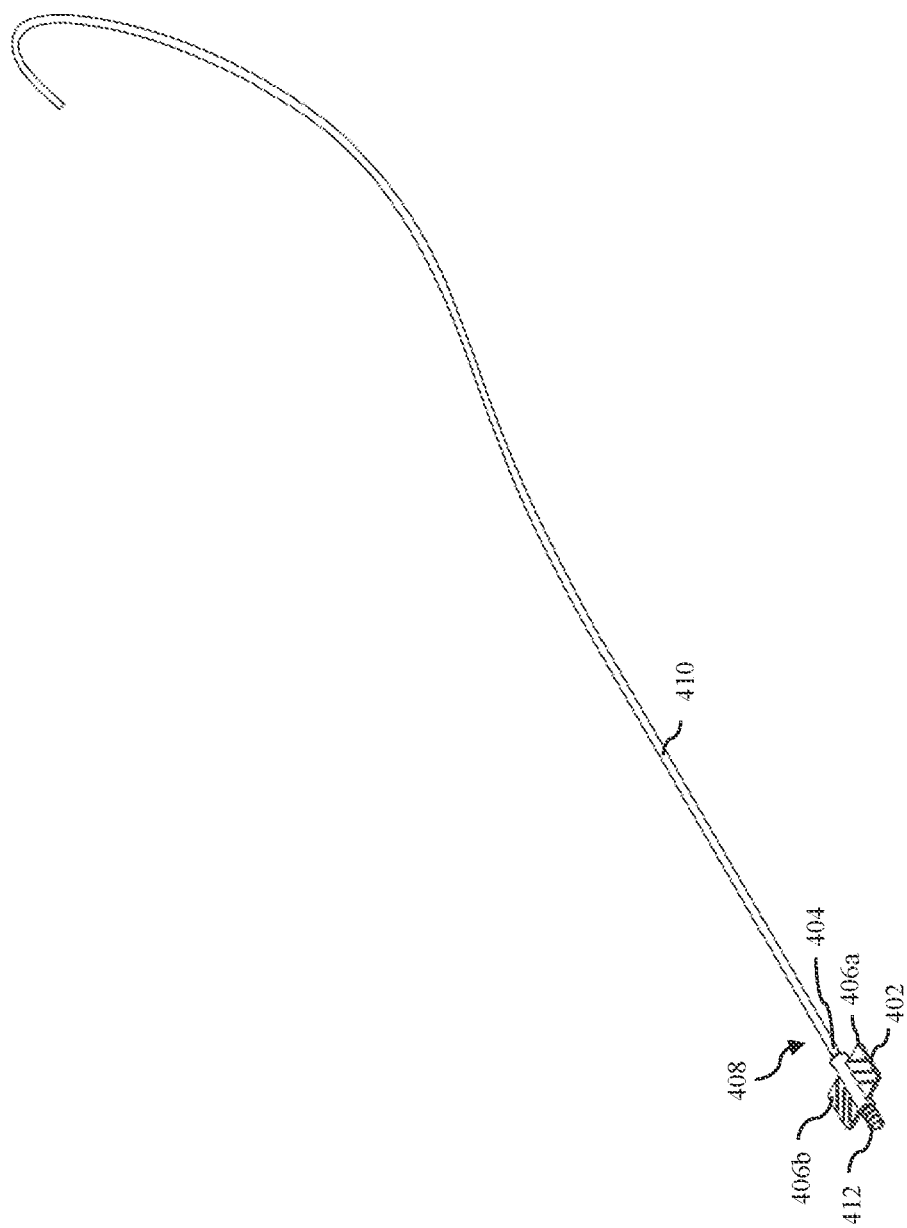
FIG. 4A is a perspective view of the second catheter for internal mammary intubation catheter extensions, according to a second example embodiment.
Figure 4B:
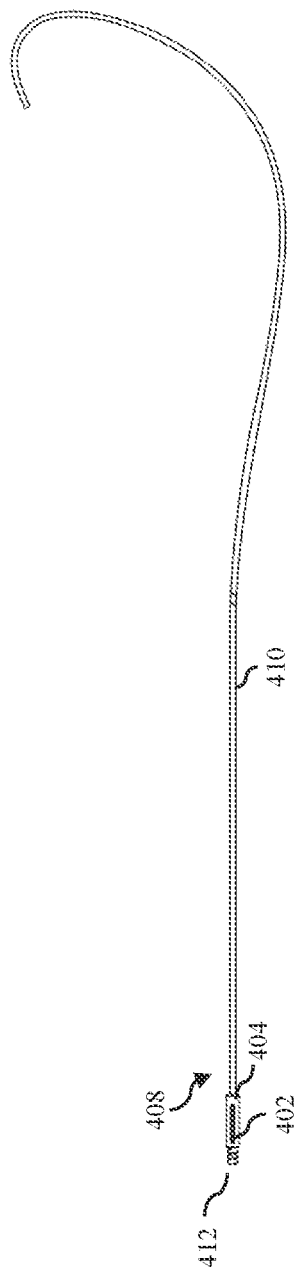
FIG. 4B is a side view of the second catheter for internal mammary intubation catheter extensions, according to a second example embodiment.
Figure 5A:
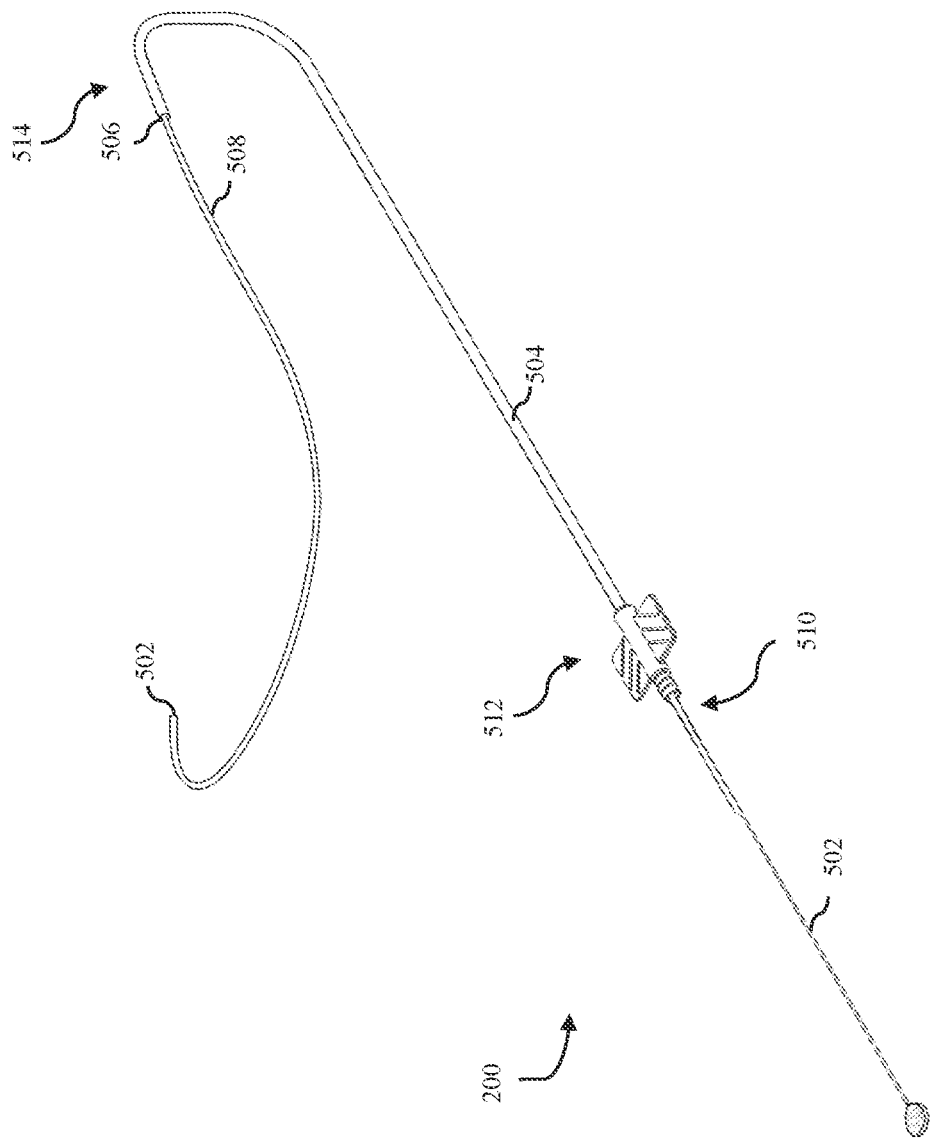
FIG. 5A is a perspective view of the second catheter proximal end for internal mammary intubation catheter extensions extending beyond the catheter distal end for subclavian artery access, according to an example embodiment.
Figure 5B:
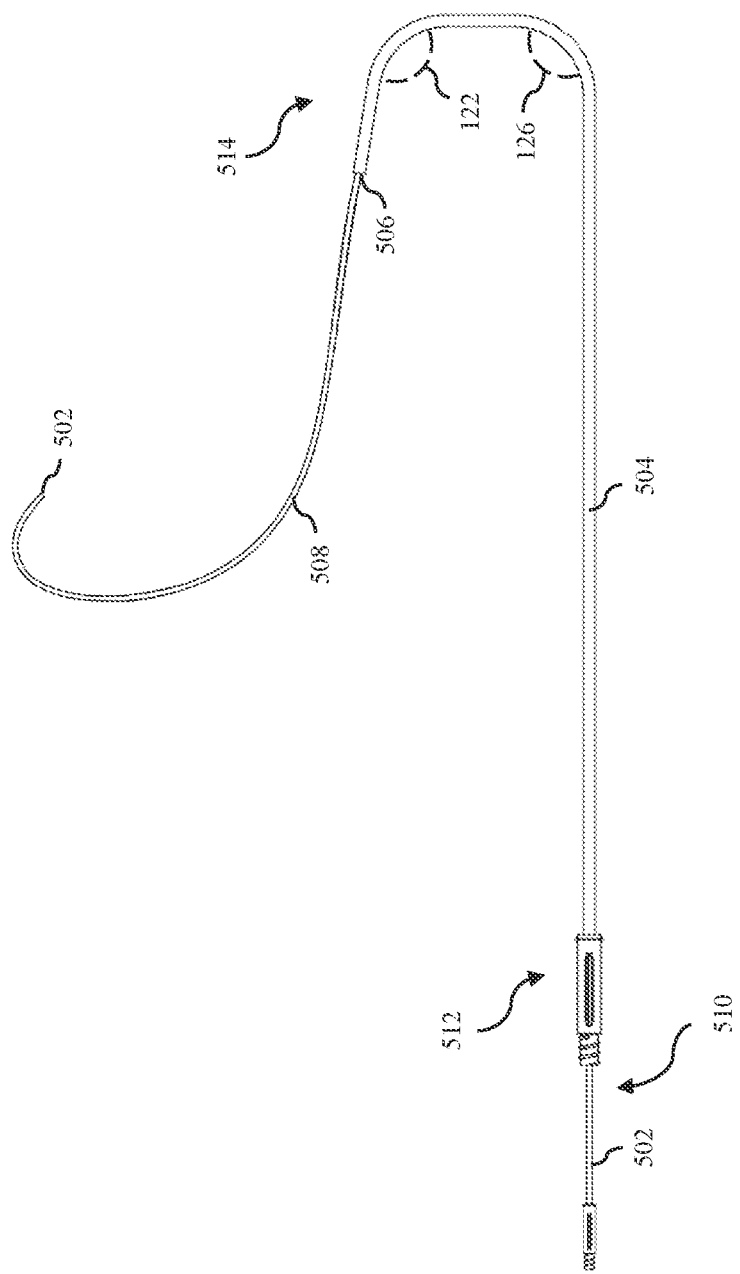
FIG. 5B is a side view of the second catheter proximal end for internal mammary intubation catheter extensions extending beyond the catheter distal end for subclavian artery access, according to an example embodiment.
Figure 6A:
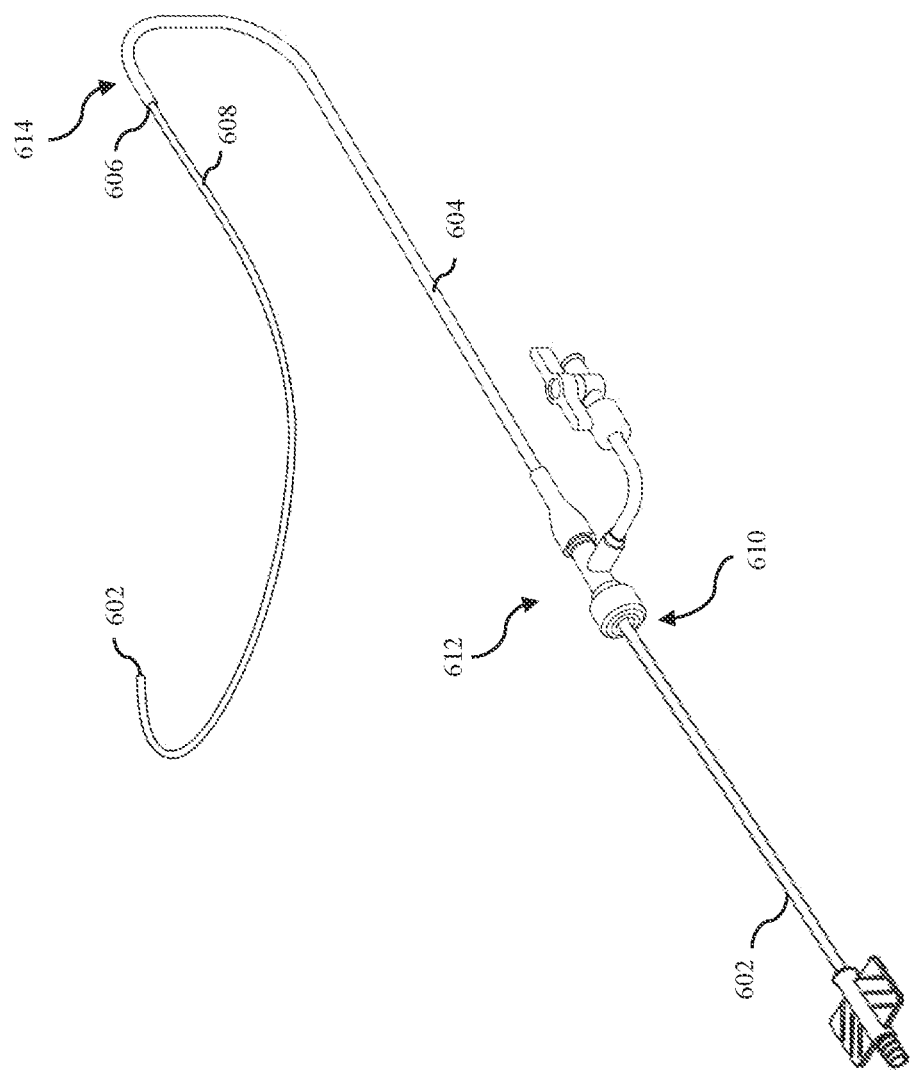
FIG. 6A is a perspective view of the second catheter distal end for internal mammary intubation catheter extensions extending beyond the catheter distal end for subclavian artery access, according to a second example embodiment.
Figure 6B:
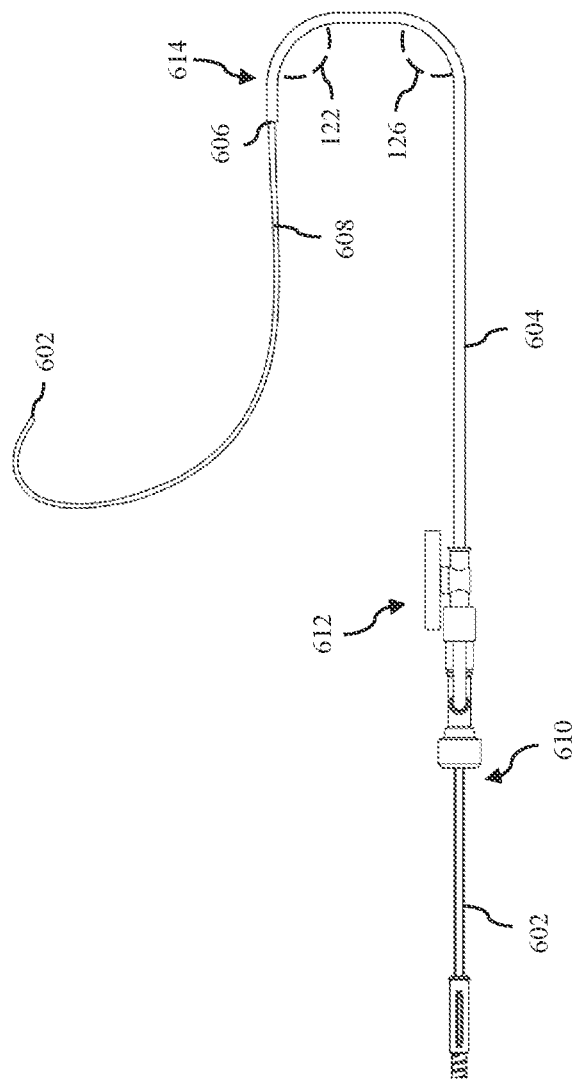
FIG. 6B is a side view of the second catheter distal end for internal mammary intubation catheter extensions extending beyond the catheter distal end for subclavian artery access, according to a second example embodiment.
Figure 7A:
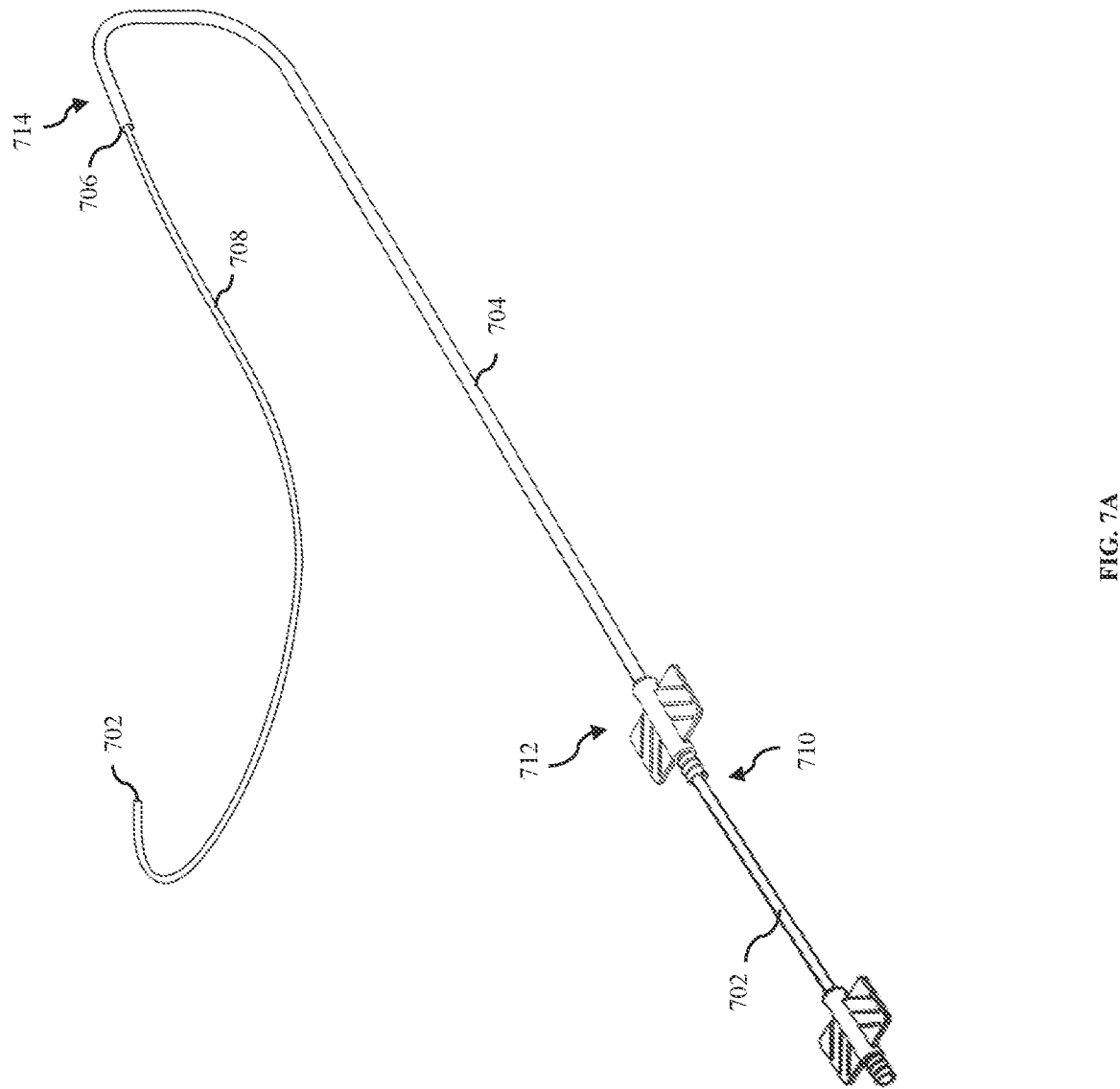
FIG. 7A is a perspective view of the second catheter distal end for internal mammary intubation catheter extensions extending beyond the catheter distal end for subclavian artery access, according to a second example embodiment.
Figure 7B:
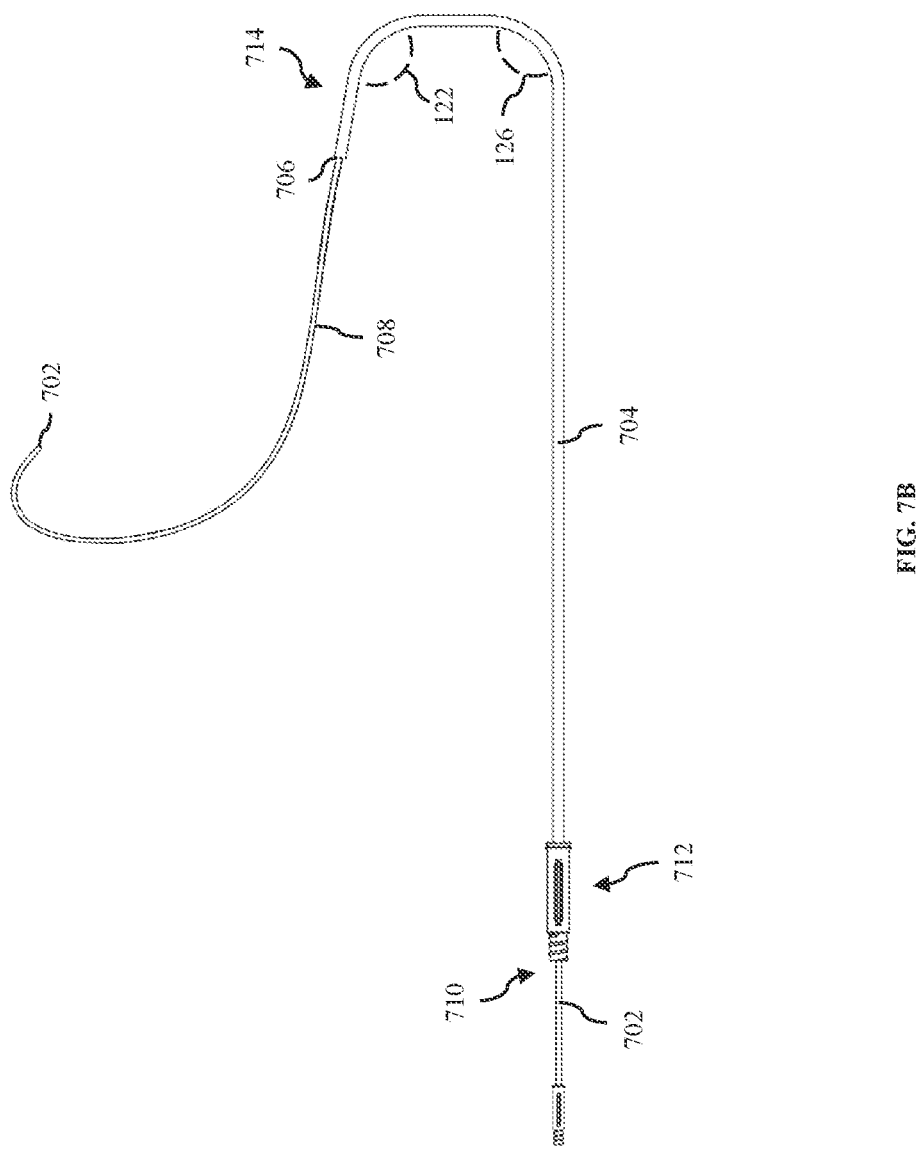
FIG. 7B is a side view of the second catheter distal end for internal mammary intubation catheter extensions extending beyond the catheter distal end for subclavian artery access, according to a second example embodiment.
Figure 8A:
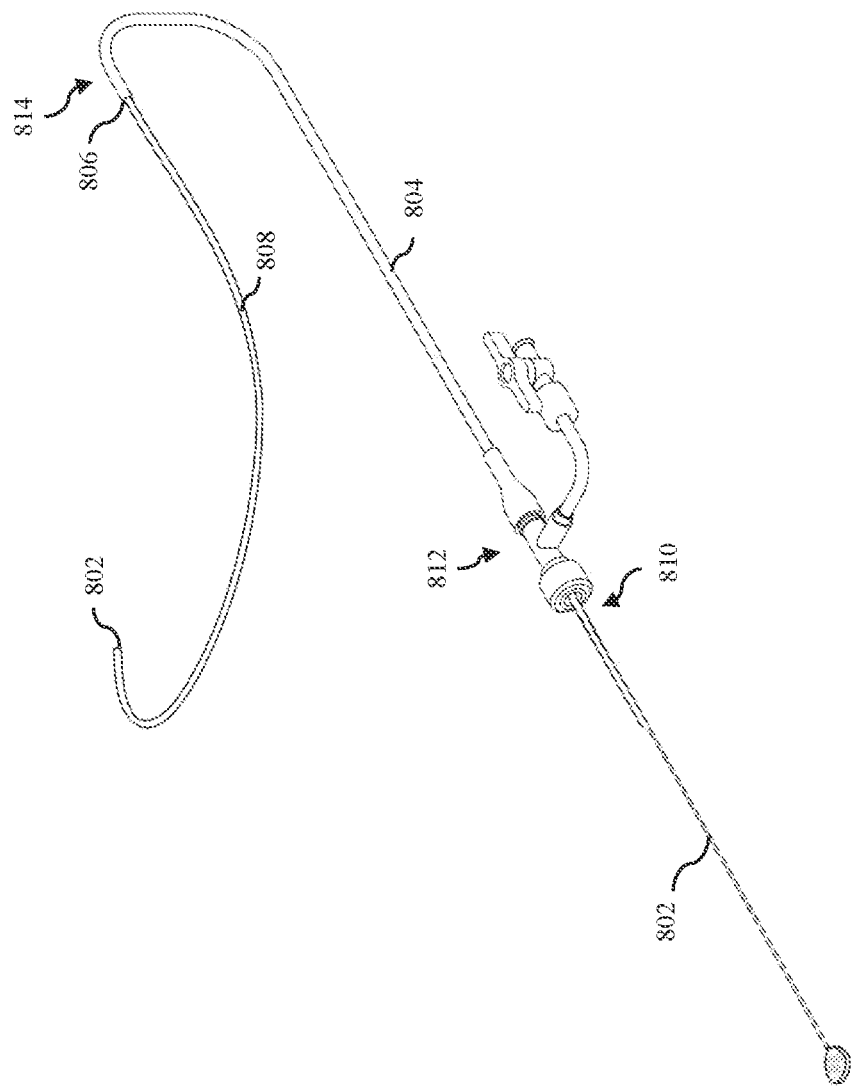
FIG. 8A is a perspective view of the second catheter distal end for internal mammary intubation catheter extensions extending beyond the catheter distal end for subclavian artery access, according to a second example embodiment.
Figure 8B:
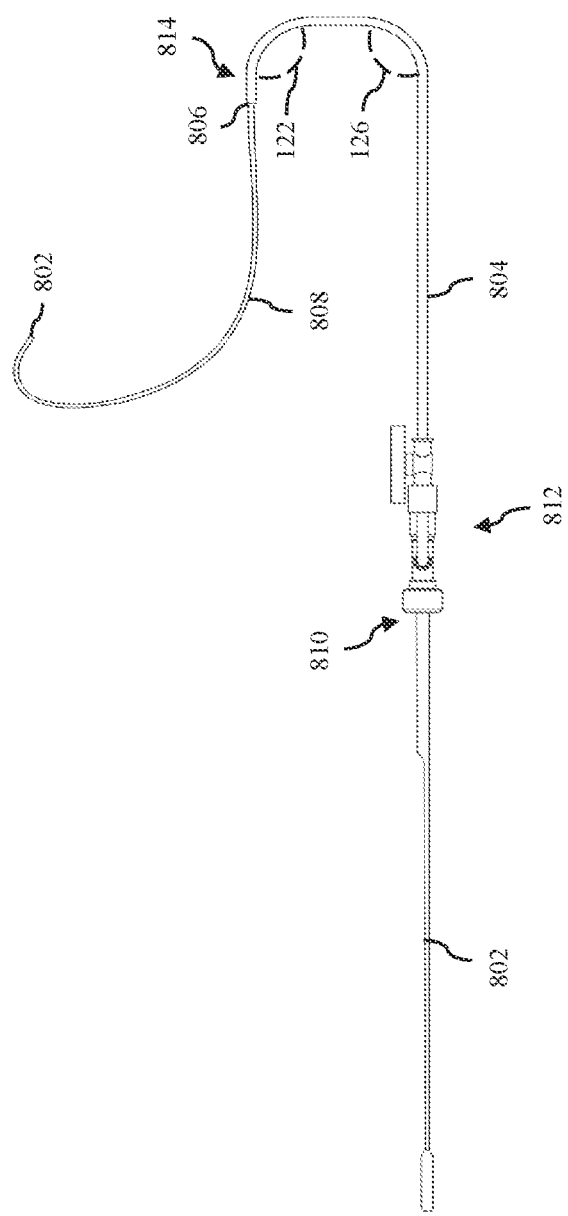
FIG. 8B is a side view of the second catheter distal end for internal mammary intubation catheter extensions extending beyond the catheter distal end for subclavian artery access, according to a second example embodiment.

Referring now to FIG. 4A and FIG. 4B, views of a second catheter for internal mammary intubation catheter extensions are shown, according to a second example embodiment. FIG. 4A is a perspective view of a second catheter for internal mammary intubation catheter extensions, according to a second example embodiment. FIG. 4B is a side view of a second catheter for internal mammary intubation catheter extensions, according to a second example embodiment. The second catheter has may include a torquing element 402 disposed proximal to a second catheter proximal terminating end 404. In certain embodiments, the torquing element may include a pair of wings (406a, 406b) extending from the perimeter of the second catheter. Each wing of the pair of torquing wings extends radially from an exterior of the elongated tubular body. In certain embodiments, the torquing element may be in attachment with the proximal end portion 408 of the second elongated tubular body 410 without having an elongated shaft. In certain embodiments, the second catheter includes a torquing element that is flat where the torquing element is in attachment with the elongated shaft. The second catheter may also include a lock hub 412 proximal to the torquing wings.

Referring now to the catheters disclosed in FIGS. 3A through 4B, a catheter system for providing radial artery access of a contralateral subclavian artery and an internal mammary artery of a patient for diagnostic and interventional angiography comprising a catheter and a second catheter, where the catheter is for introducing the second catheter into the patient. The catheter system comprises the catheter of FIG. 3 and the second catheter of FIG. 4. A method for utilizing the catheter system during coronary angiography and interventional procedures is as described herein, according to a second example embodiment. From the right radial artery access, a 0.035 exchange wire is inserted into the patient from the right radial access point and advanced into the ascending aorta. Once in the ascending aorta, using general techniques, the exchange wire is then directed into the proximal descending aorta. First the catheter (illustrated in FIG. 3) for subclavian artery access is flushed and purged via the second elongated tubular body. The catheter is advanced over the exchange wire into the proximal descending aorta beyond the ostium of the left subclavian artery. The catheter is then purged, cleared, and connected in accordance with standard medical practice. In some embodiments, the use of a Touhy-Borst device is used to prevent backflow of fluid in the catheter where the Touhy-Borst device is connected to the lock hub on the second elongated tubular body lumen. Then the catheter is slowly withdrawn until is falls into the left subclavian ostium such that the first arm advances into the left subclavian artery. The exchange wire is then advanced antegrade into the subclavian artery. The catheter is then either advanced or withdrawn a few millimeters to position the catheter in the vessel coaxially in the right to left projection such that the first arm is positioned coaxially to the left subclavian artery. By rotating the torquing element, the first arm and the second arm are rotated to position either catheter anterior or posterior. The torquing element can rotate the catheter either clockwise or counterclockwise. The exchange wire is then removed. Now, selective angiography and intervention of at least one of the left subclavian, axillary, and the left vertebral arteries can be performed in accordance with standard procedure. Selective angiography and intervention can be performed on the entire left upper extremity from this position.

To sub-selectively cannulate the left internal mammary artery, the exchange wire is re-inserted into the catheter and advanced out into the distal subclavian artery. Ensure that a Touhy-Borst device is attached to the hub of the catheter. The second catheter for internal mammary intubation (illustrated in FIG. 4) is inserted into the patient through the radial artery access. The second catheter receives the exchange wire such that the catheter is inserted into the patient over the exchange wire and through the catheter for subclavian artery access. The second catheter is then advanced into the left subclavian artery extending beyond the terminal end of the catheter for subclavian artery access. The second catheter is advanced within the left subclavian artery beyond the left internal mammary artery ostium. By rotating the torquing element, the second preformed tubular hook element is rotated to position either catheter anterior or posterior to effectively intubate the ostium of the left internal mammary artery. The exchange wire is then removed. The catheter is then purged, cleared, and connected in accordance with standard medical practice. Now, selective angiography and intervention of the left internal mammary artery can be performed in accordance with standard procedure.

The methods for utilizing the catheter system during coronary angiography and interventional procedures for left radial access to the right subclavian, right internal mammary artery, and the right carotid artery is within the spirt and scope of the disclosure and is a reflective procedure of the aforementioned methods, according to the second example embodiment. It is understood that the catheter and catheter systems disclosed herein can allow angiography and intervention of the entire left and right upper extremities. The disclosed method is not limited to angiography and intervention of the subclavian and internal mammary arteries. In other embodiments, the method may include advancing at least one of the catheter and second catheter into at least one of the right brachiocephalic artery, the right subclavian artery, the right carotid artery, the left subclavian artery, the left vertebral artery, the left carotid artery, the bilateral renal arteries, mesenteric arteries, and the bilateral iliac and femoral arteries. Access to each artery depends on whether the catheter was inserted through the radial access of the right radial artery or the left radial artery. Through the use of the catheter system, coronary and interventional procedures can be performed on the entire right and left upper extremities.

Referring now to FIGS. 5A through 8B, views of a second catheter distal end for internal mammary intubation catheter extensions extending beyond the catheter distal end for subclavian artery access is shown, according to four example embodiments. The second catheter (502, 602, 702, 802) receives an exchange wire such that the catheter is inserted into the patient over the exchange wire and through the catheter (504, 604, 704, 804) for subclavian artery access. The catheter receives the second catheter at an opening (510, 610, 710, 810) on the proximal end (512, 612, 712, 812) of the catheter. The opening may be through at least one of the elongated tubular body, lock hub, Touhy-Borst device, second elongated tube, stop cock, etc.

The second catheter is then advanced into the left subclavian artery and extends beyond the terminal end (506, 606, 706, 806) of the catheter at the catheter distal end (514, 614, 714, 814) for subclavian artery access. The second catheter is advanced within the left subclavian artery beyond the left internal mammary artery ostium. The catheter acts as a guide for the second catheter to enter the internal mammary arteries. The second catheter is coated with a lubricous coating (508, 608, 708, 808) which reduces the coefficient of friction between the catheter and the second catheter. The lubricious coating further enables the physician to reach more distal regions and to cross difficult lesions, reduced procedure time, reduces insertion forces, increases patient comfort, enhances the ability to maneuver tortuous paths such as the ostium of the subclavian artery and the internal mammary artery, provides more precise push and torque control, and reduces tissue irritation and damage. In other embodiments, both the outer surface and inner surface of the catheter and the second catheter are coated with a lubricious coating. Standard lubricious coatings for medical devices are within the spirit and scope of the disclosure. The lubricous coating may be on the first leg and the second leg to allow the catheter to easily traverse the ostium of at least the left subclavian and allow it to easily advance through the respective artery to position the catheter coaxially with the artery.

Figure 9:
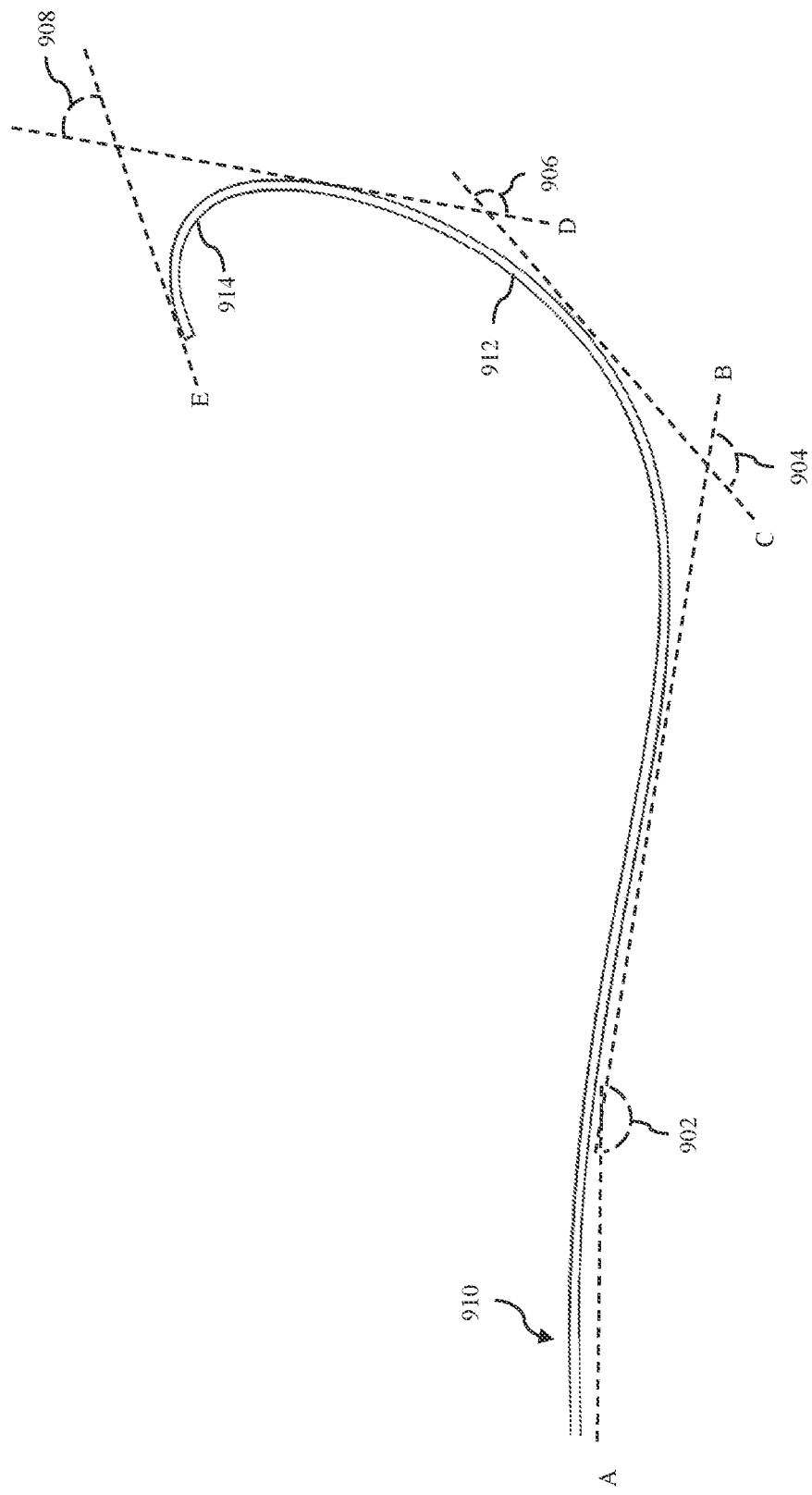
FIG. 9 is a side view of the second preformed tubular hook element of the second catheter illustrating the angles, according to an example embodiment.

Referring now to FIG. 9, a side view of the second preformed tubular hook element of the second catheter illustrating the angles is shown, according to an example embodiment. The second catheter preformed tubular hook element includes a third angle 902, fourth angle 904, a fifth angle 906, and a sixth angle 908. The third angle is defined by line A and line C such that both lines connect where the second catheter distal end portion 910 and the second preformed tubular hook element 912 meet. The third angle may be between 155 to 185 degrees, and ideally approximately 170 degrees; however, other angles may be used within the spirit and scope of the present invention. The fourth angle 904 is defined by line B and line C. The fourth angle begins the curve of the second preformed tubular hook element. The fourth angle may be 130 to 155 degrees, and ideally 145 degrees; however, other angles may be used within the spirit and scope of the present invention. The fifth angle 906 is defined by line C and line D. The fifth angle may be 115 to 145 degrees, and ideally, 130 degrees; however, other angles may be used and are within the spirit and scope of the present invention. The sixth angle 908 is defined by line D and line E such that the sixth angle defines an end curve 914 of the second catheter preformed tubular hook element. The end curve allows the second catheter to fit into the ostium of the internal mammary artery as it advances through the subclavian artery. The end curve has the arch of a circle with a diameter of 1.5 centimeters to 3 centimeters. The sixth angle may be 90 degrees to 120 degrees; however, other angles may be used and are within the spirit and scope of the present invention.

With reference to FIGS. 10-21, an anatomical view of a heart is illustrated showing the catheter and the second catheter in use during medical procedure. It is understood that the catheter system and the heart are not to scale. It is further understood that the figures serve to provide an illustration of the catheter system as used during medical procedure to show how the system improves upon the prior art. Moreover, it is understood that the measurements of the catheter and the second catheter as described herein are according to an example embodiment and may vary within the spirt and scope of the disclosure. In each of FIGS. 10-21, a diagram illustrating the catheter, second catheter, and exchange wire in an exemplary anatomy of a patient's heart at various steps is shown, according to an example embodiment. The diagrams illustrate the medical procedure as being conducted through the right radial artery access, advancing into the left subclavian and left internal mammary arteries. It is understood that embodiment illustrated herein can be performed form the left radial artery access, advancing into the right subclavian and right internal mammary arteries.

Figure 10:
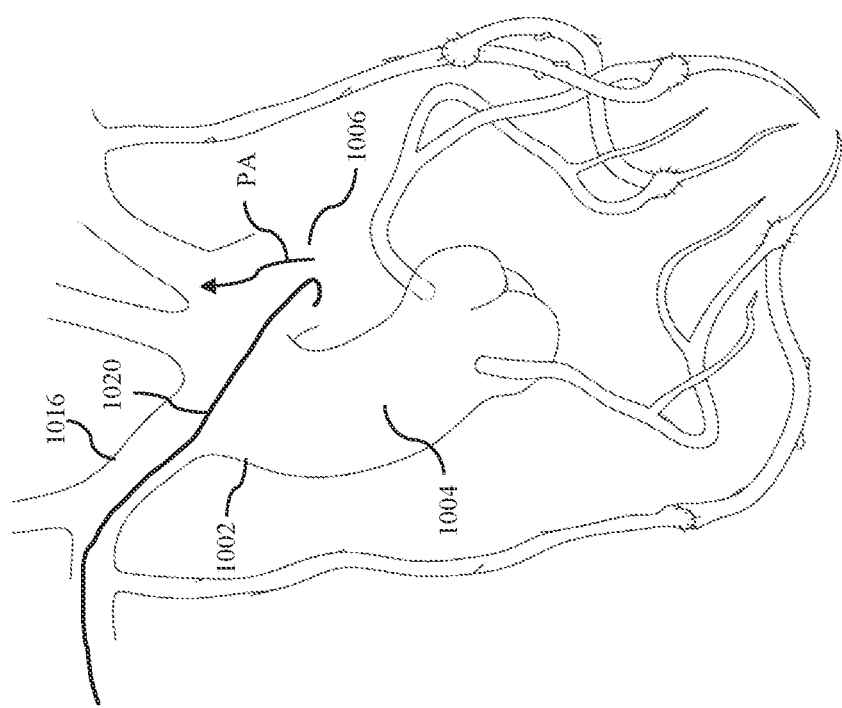
FIG. 10 is an anatomical diagram illustrating an exchange wire inserted in the patient's heart, according to an example embodiment.

FIG. 10 illustrates the guide wire or exchange wire being advanced from the radial artery 1016 into the aorta 1002, specifically in this example embodiment, the descending aorta 1006. In other embodiments, such as a reverse procedure from the left radial artery, the guide wire will advance into the ascending aorta 1004. As shown, the arrow PA, illustrates the prior art which has the exchange wire inserted through the femoral artery into the descending aorta. The present embodiment improves upon the prior art by allowing the procedure to be efficiently performed through a radial artery access, thereby decreasing the time needed for surgery, procedural risks, and patient recovery.

Figure 11:
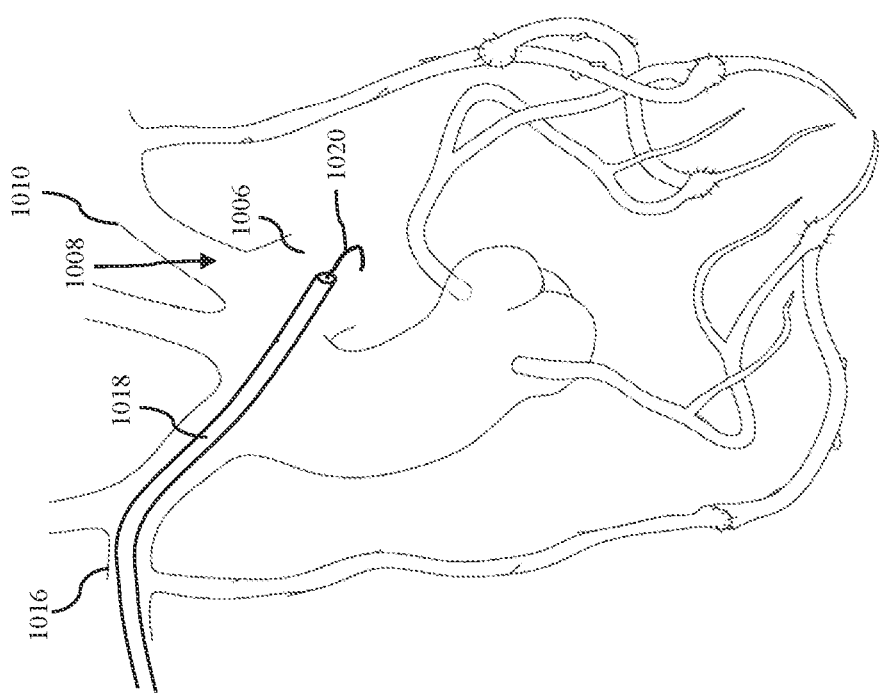
FIG. 11 is the anatomical diagram illustrating the catheter guided over the exchanged wire in the patient's heart, according to an example embodiment.

In the diagram shown in FIG. 11, the catheter 1018 received the exchange wire 1020 through the tubular body at the distal end. The tubular body of the catheter ideally has an inner diameter of approximately 1.8 millimeters and an outer diameter of 2.08 mm such that the inner diameter is configured to receive the exchange wire and the second catheter. In any such embodiment, the inner diameter of the catheter is larger than the outer diameter of the second catheter. The catheter was advanced through the radial access into the aorta. Because the catheter is made of flexible, resilient materials, comprising materials such as a lubricious polytetrafluoroethylene, inner layer, a stainless-steel braided wire layer, and/or a nylon elastomer blend jacket-outer layer, the catheter may be prevented from taking the preformed hook shape while the guide wire is within curved portions of the catheter. It is understood that the catheter may be made out of various materials consistent with standard medical practice and technology within the spirit and scope of the disclosure. The lubricious coating may be on the inner surface of the tubular body and/or the outer surface of the catheter to allow the system to smoothly receive the guide wire and second catheter and advance throughout the arterial system. Moreover, the length of the catheter and/or the tubular body, is ideally 78-83 cm. In certain embodiments length of the catheter is measure from the from each terminating end of the catheter as if the catheter was straightened out. In other embodiments, the length of the catheter may be measured from the proximal end of the elongated tubular body to the distal end of the elongated tubular body.

FIG. 11 shows the catheter 1018 advanced into the descending aorta 1006 past the ostium 1008 of the subclavian artery 1010. At this position within the heart, the guide wire is slightly withdrawn until before the distal end portion of the elongated tubular body, specifically, before the second curve of the catheter. If positioned correctly within the descending aorta 1006 in FIG. 11, then the catheter will take the preformed hook shape such that the resilient properties of the catheter allow the first arm to be at the optimal first angle to enter the ostium 1008 of the subclavian artery 1010. This is shown in FIG. 13. Otherwise, the catheter will have the preformed hook within the aorta 1002. This is shown in FIG. 12.

Figure 12:
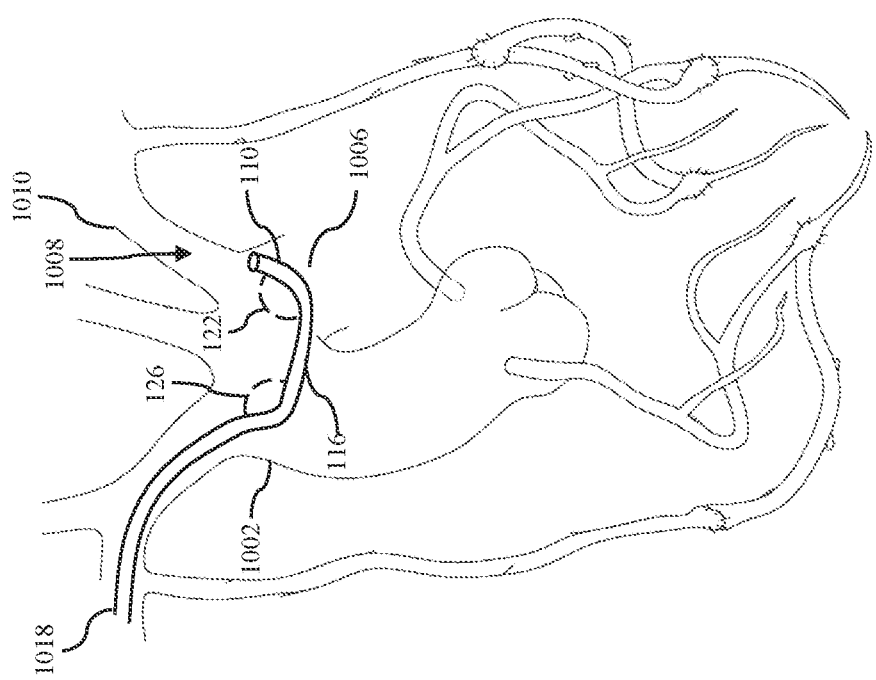
FIG. 12 is the anatomical diagram illustrating the exchange wire partially withdrawn allowing the catheter to engage the hook shape of the catheter in the patient's heart, according to an example embodiment.
Figure 13:
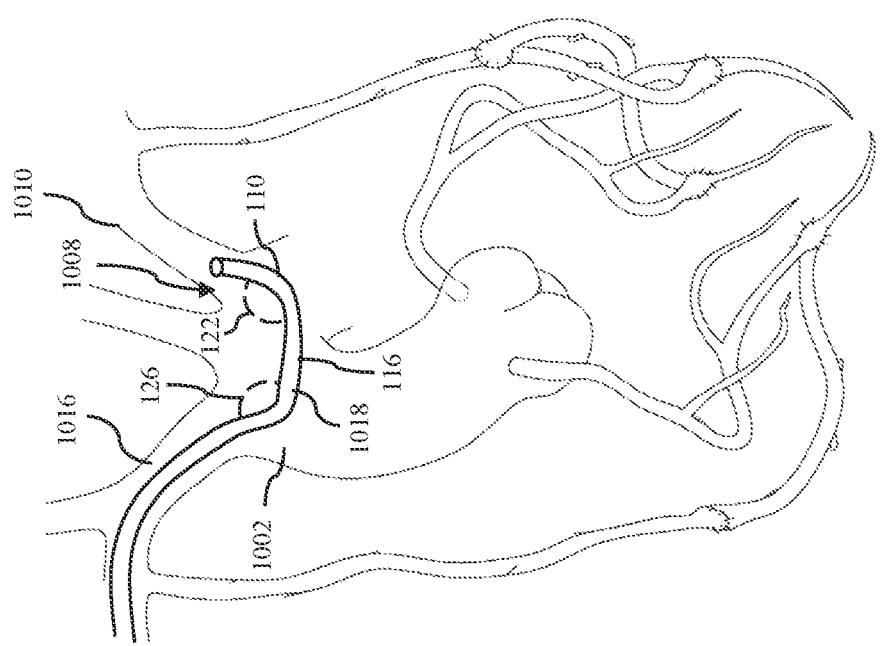
FIG. 13 is the anatomical diagram illustrating the catheter entering the ostium of the left subclavian artery in the patient's heart, according to an example embodiment.
Figure 14:
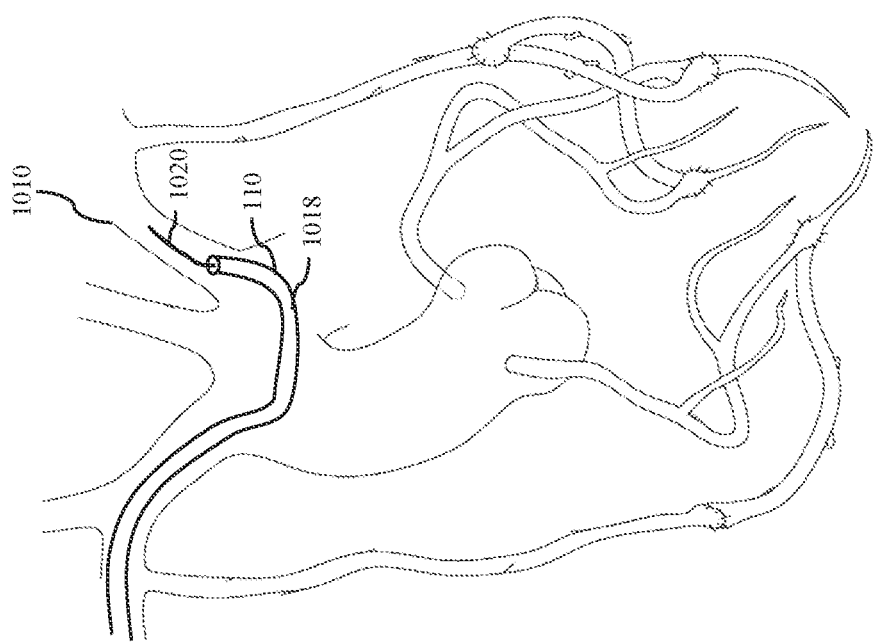
FIG. 14 is the anatomical diagram illustrating the exchange wire advanced into the subclavian artery of the patient's heart to coaxially align the catheter, according to an example embodiment.

In FIG. 12, the catheter 1018 should be slightly withdrawn to allow the terminating end of the first arm 116 to enter the ostium 1008 of the subclavian 1010. The first arm may be between 4-6 centimeters in length. The first angle or curve 122 in one embodiment is between 90 and 120 degrees. Similarly, the second arm may be between 3 to 6 cm. In one embodiment, the second angle or curve between 100 to 120 degrees. The length for the first and/or second arm is configured to optimize the procedure to reduce risks depending on the person being operated on.

FIG. 13 is the desired configuration of the catheter 1018 within the heart. It is clearly shown that the elongated tubular body has the second curve 126 being between ideally 100 to 120 degrees connecting to the second arm 116. The second arm is at an optimal length between 3 to 6 cm to allow the first curve 122 to be ideally between 90 to 120 degrees in its preformed hook shape. This allows the first arm 110 to enter the ostium 1008 of the subclavian 1010 as shown. This catheter allows the preformed hook to provide an operational channel from the radial artery to the subclavian through the aortic arch. As illustrated, the preformed tubular hook is shown to bend from the second curve extending out of the radial artery 1016 and bending, via the first curve, into the opening or ostium of the subclavian. The second arm spans through the aortic arch.

Figure 15:
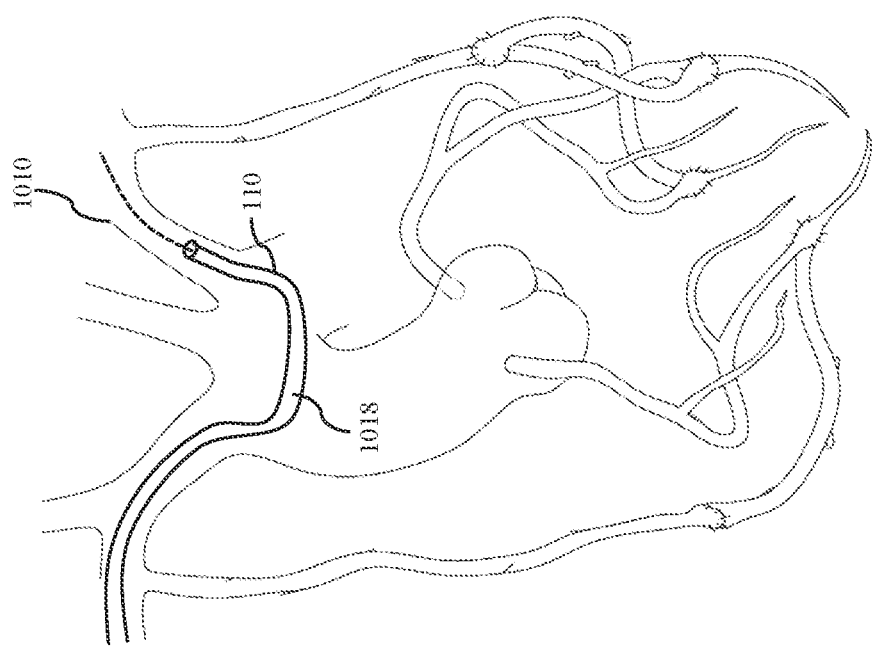
FIG. 15 is the anatomical diagram illustrating the catheter coaxially aligned within the subclavian artery such that standard procedure for angiography and intervention can be performed, according to an example embodiment.

If the first arm 110 does not automatically align coaxially within the subclavian artery 1010, meaning the centerline axis of the first arm is substantially parallel with the subclavian artery, then the guide wire 1020 is reintroduced (shown in FIG. 14) to coaxially align the first arm. When the first arm is coaxially aligned (shown in FIG. 15 represented by the dotted line), the guide wire is withdrawn. The exchange wire is then removed. The catheter 1018 is then purged, cleared, and connected in accordance with standard medical practice. Then, selective angiography and intervention the subclavian can be performed in accordance with standard procedure.

Figure 16:
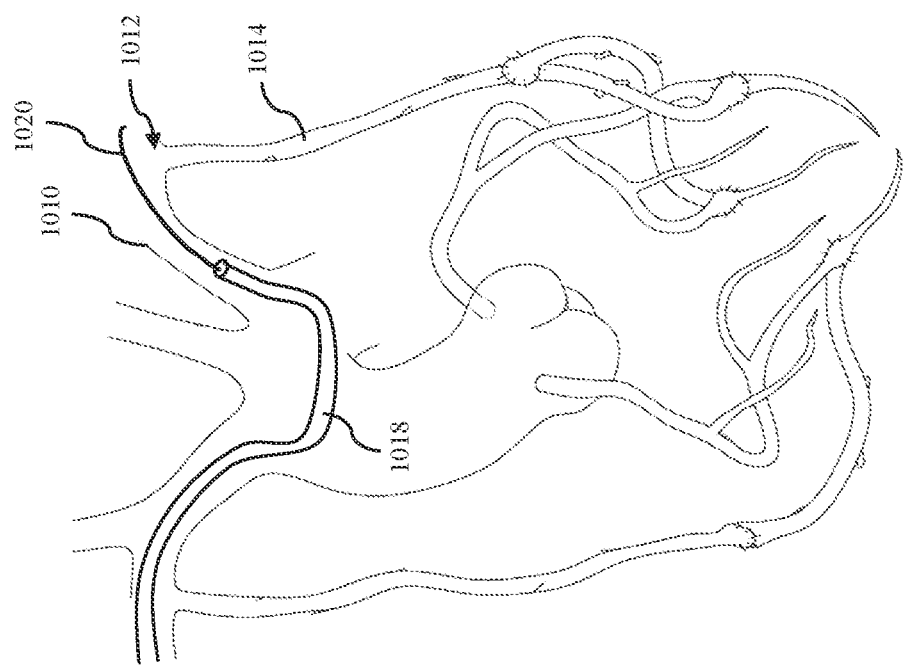
FIG. 16 is the anatomical diagram illustrating the exchange wire re-inserted into the catheter and advanced into a distal subclavian artery of the patient's heart, according to an example embodiment.
Figure 17:
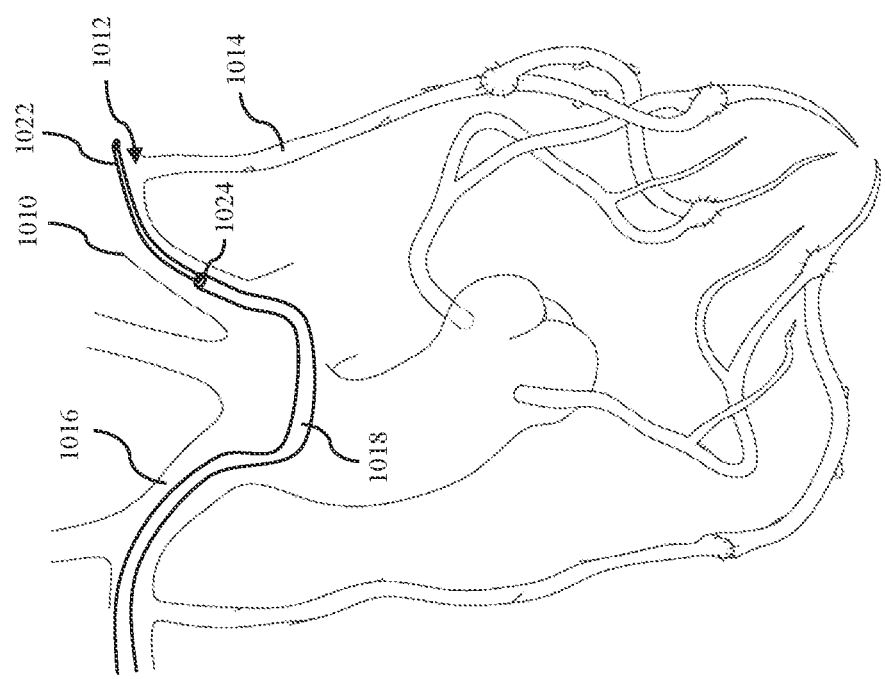
FIG. 17 is the anatomical diagram illustrating the catheter receiving the second catheter which is inserted over the exchange wire and advanced past the terminating end of the catheter in the subclavian artery, according to an example embodiment.

To sub-selectively cannulate the left internal mammary artery, the exchange wire 1020 is re-inserted into the catheter 1018 and advanced out into the distal subclavian artery 1010 past the ostium 1012 of the internal mammary artery 1014 (shown in FIG. 16). The second catheter 1022 is then inserted into the proximal end of the elongated tubular body of the catheter over the exchange wire 1020, past the terminating end 1024 of the catheter, and past the ostium 1012 of the internal mammary artery 1014 as shown in FIG. 17. The second catheter has an outer diameter smaller than the inner diameter of the catheter and an inner diameter larger than the diameter of the guide wire. Ideally, the inner diameter of the second catheter is approximately 1.42 mm, and the outer diameter of the second catheter is 1.7 mm. However, other diameters may be used that are within the spirit and scope of the present invention.

Figure 18:
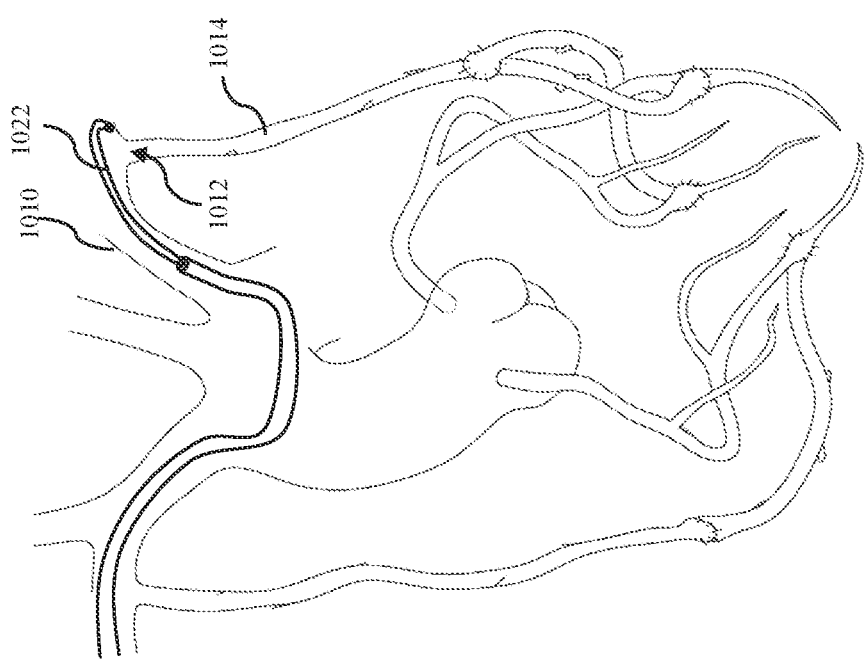
FIG. 18 is the anatomical diagram illustrating second catheter having the preformed hook shape in the subclavian artery when the exchange wire is withdrawn, according to an example embodiment.
Figure 19:
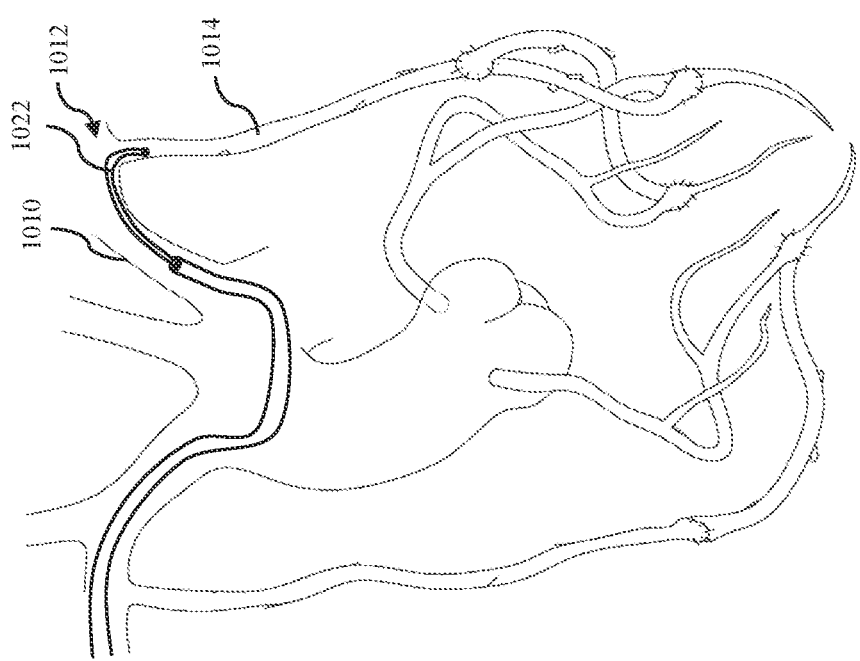
FIG. 19 is the anatomical diagram illustrating the second catheter in the ostium of the internal mammary artery, according to an example embodiment.

Once the second catheter is past the ostium 1012 of the internal mammary artery 1014, then the guide wire is withdrawn to at least one of (i) before the second tubular hook of the second catheter, and (ii) before the distal end portion of the second catheter. If the second catheter is positioned correctly during procedure, then once the guide wire is removed, then the second preformed hook should take form such that the distal end portion of the second catheter enters the ostium 1012 of the internal mammary artery 1014 as shown in FIG. 19. Otherwise, the second catheter will have the preformed hook shape within the subclavian as shown in FIG. 18. The second catheter would then need to be slightly withdrawn to allow the preformed hook to fall into the ostium 1012 as shown in FIG. 19.

Figure 20:
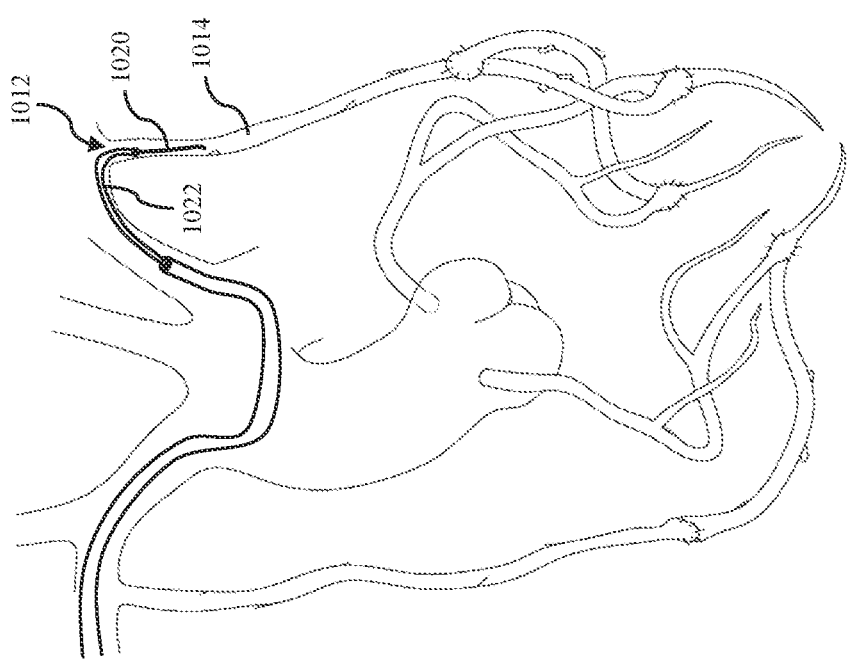
FIG. 20 is the anatomical diagram illustrating the exchange wire coaxially aligning the second catheter within the internal mammary artery, according to an example embodiment.
Figure 21:
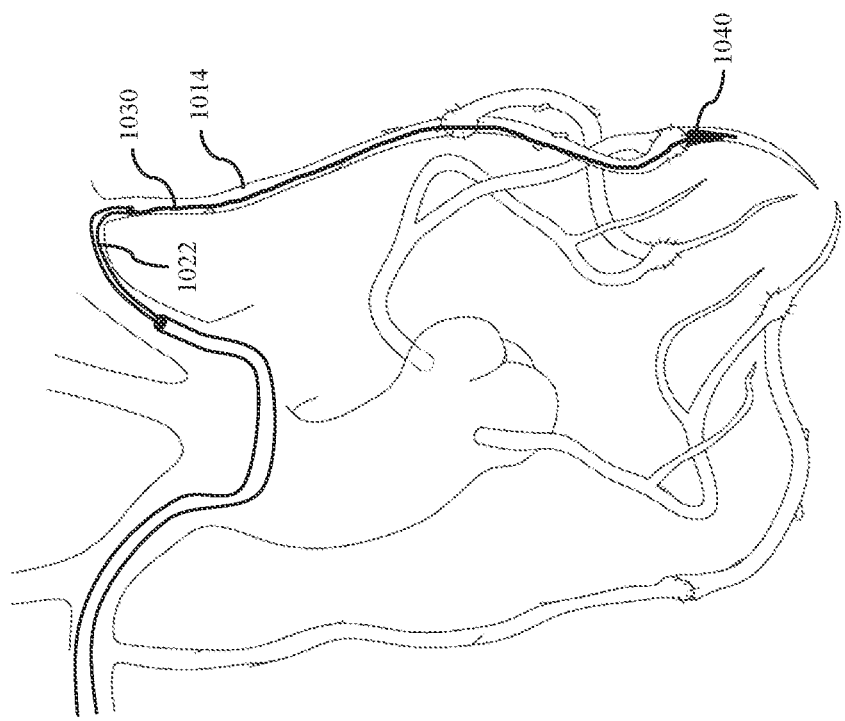
FIG. 21 is the anatomical diagram illustrating standard medical practice, such as balloon angioplasty or stent, according to an example embodiment.

Ideally, the second catheter 1022 will be coaxially aligned with the internal mammary artery 1014 when the second preformed hook advances into the internal mammary artery 1014. However, the guide wire 1020 may be reinserted, as shown in FIG. 20, ad advanced antegrade into the internal mammary artery to align the second catheter coaxially within the artery such that the catheter is positioned in the same direction and along the same axis as that of the internal mammary artery. The catheter is then purged, cleared, and connected in accordance with standard medical practice. Now, selective angiography and intervention of the left internal mammary artery can be performed in accordance with standard procedure. FIG. 21 is an exemplary embodiment of medical procedure, such as coronary angioplasty. Shown is a coronary wire 1030 of 0.0014 inches in diameter, inserted into the tubular channel of the second catheter and advanced into the internal mammary artery 1014 to provide a balloon stent 1040. This two-catheter system improves upon the prior art by providing a continuous operational channel from the radial artery to the internal mammary artery through the subclavian artery such that a trained medical professional may perform diagnostic and interventional angiography from the radial access. Please note that the catheter 1018 and second catheter 1022 described herein may be any embodiment of the catheter and second catheter as detailed and described within the spirit and scope of the disclosure.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

I claim:
1. A catheter for providing access to a contralateral subclavian artery from a radial artery access, wherein the catheter is for introducing a second catheter into a patient that provides access to an internal mammary artery of the patient for diagnostic and interventional angiography, wherein the catheter is preformed and comprises an elongated tubular body being substantially straight and having a proximal end portion and a distal end portion, wherein the distal end portion is contiguous to a preformed tubular hook element, the preformed tubular hook element comprising:
   a substantially straight first arm proximal to a terminating end of the catheter; and
   a substantially straight second arm contiguous to the first arm through a curve connecting the first arm to the second arm, and wherein the second arm is contiguous to the distal end portion of the elongated tubular body through a second curve connecting the second arm to the distal end portion of the elongated tubular body.

2. The catheter of claim 1, wherein the elongated tubular body has an elongated tubular body length of approximately at least 90 cm.

3. The catheter of claim 1, wherein the curve has a first angle between approximately 100 to 120 degrees.

4. The catheter of claim 1, wherein the first arm has a first arm length of at least 4 cm.

5. The catheter of claim 1, wherein the second curve has a second angle between approximately 100 to 120 degrees.

6. The catheter of claim 1, wherein the second arm has a second arm length between 3 cm to 6 cm.

7. The catheter of claim 1, wherein the catheter further comprises a lock hub at the proximal end portion of the elongated tubular body.

8. The catheter of claim 1, wherein a hemostatic diaphragm is disposed at the proximal end portion of the elongated tubular body.

9. The catheter of claim 1, wherein a second elongated tubular body, having a second elongated tubular body lumen, is connected to the proximal end portion of the elongated tubular body such that the second elongated tubular body lumen is in fluid communication with a first elongated tubular body lumen of the elongated tubular body.

10. The catheter of claim 1 further comprising:
    wherein the curve has an angle between approximately 90 to 130 degrees relative between the first arm and the second arm; and
    wherein the second curve has a second angle between 90 to 130 degrees relative between the second arm and the elongated tubular body.

11. A catheter system for providing access to a contralateral subclavian artery and to an internal mammary artery from a radial artery access for diagnostic and interventional angiography, the catheter system comprising:
    a. a preformed first catheter comprising:
       i. an elongated tubular body being substantially straight having a distal end portion, a proximal end portion and a lumen, and wherein the distal end portion is contiguous to a preformed tubular hook element;
       ii. the preformed tubular hook element extending from the distal end portion of the elongated tubular body;
       iii. a substantially straight first arm proximal to a terminating end of the first catheter;
       iv. a substantially straight second arm contiguous to the first arm through a curve connecting the first arm to a second arm, and wherein the second arm is contiguous to the distal end portion of the elongated tubular body through a second curve connecting the second arm to the distal end portion of the elongated tubular body
    b. a performed second catheter comprising:
       i. a second catheter elongated tubular body having a second catheter distal end portion and a second catheter proximal end portion;
       ii. a second preformed tubular hook element extending from the second catheter distal end portion; and
       iii. wherein at least the second preformed tubular hook element is configured to pass through the first catheter.

12. The catheter system of claim 11 wherein the second catheter comprises the second catheter elongated tubular body having the second catheter proximal end portion and the second catheter distal end portion, wherein the second catheter distal end portion is contiguous to the second preformed tubular hook element, the second preformed tubular hook element comprising:
    i. a substantially straight first portion contiguous to the second catheter distal end portion of the second catheter elongated tubular body through a first curve having a first angle between 155 to 185 degrees;
    ii. a second portion contiguous to the first portion through a second curve having a second angle between 130 to 155 degrees;
    iii. a third portion contiguous to the second portion through a third curve having a third angle between 115 to 145 degrees; and
    a fourth portion contiguous to the third portion through a fourth curve having a fourth angle between 90 to 120 degrees; wherein the fourth portion defines a terminating end of the second catheter.

13. The catheter system of claim 12, wherein the second catheter has a second catheter length of approximately 110 cm.

14. The catheter system of claim 13, wherein the second catheter comprises a lubricous coating covering at least a portion of a second catheter exterior of the second catheter for reducing friction between the second catheter exterior and a at least a portion of a first catheter interior of the first catheter.

15. The catheter system of claim 14, wherein the second catheter further comprises an elongated shaft disposed between a second catheter proximal terminating end and a second catheter proximal end portion.

16. The catheter system of claim 15, wherein the elongated shaft of the second catheter has a shaft length between 50 cm to 70 cm.

17. A catheter for providing access to a contralateral subclavian artery from a radial artery access, wherein the catheter is for introducing a second catheter into a patient that provides access to an internal mammary artery of the patient for diagnostic and interventional angiography, wherein the catheter is preformed and consists of:
    an elongated tubular body being substantially straight and having a distal end portion and a proximal end portion;
    a preformed tubular hook element contiguous with and extending from the distal end portion of the elongated tubular body, wherein the preformed tubular hook element consists of:
    a substantially straight first arm proximal to a terminating end of the catheter;
    a substantially straight second arm contiguous to the first arm through a curve connecting the first arm to the second arm, and wherein the second arm is contiguous to the distal end portion of the elongated tubular body through a second curve connecting the second arm to the distal end portion of the elongated tubular body;

wherein the curve has an angle between approximately 100 to 120 degrees relative between the first arm and the second arm;

wherein the second curve has a second angle between 100 to 120 degrees relative between the second arm and the elongated tubular body;

wherein the first arm has a first arm length of at least 4 cm; and wherein the second arm has a second arm length between 3 cm and 6 cm.

18. The catheter of claim 17, wherein the elongated tubular body has an elongated tubular body length of at least 90 cm.

19. The catheter of claim 18, wherein the preformed tubular hook element is preformed such that it is configured to enter the ostium of the contralateral subclavian artery and advance the first arm coaxially within the contralateral subclavian artery when the catheter is disposed within the radial artery and the aorta.

\* \* \* \* \*